(12) United States Patent
Takahashi

(10) Patent No.: US 10,682,842 B2
(45) Date of Patent: Jun. 16, 2020

(54) METHOD FOR PRODUCING GELATIN STRUCTURE, AND GELATIN STRUCTURE PRODUCTION SYSTEM

(71) Applicant: FUJIFILM Corporation, Tokyo (JP)

(72) Inventor: Kazunori Takahashi, Ashigarakami-gun (JP)

(73) Assignee: FUJIFILM Corporation, Minato-ku, Tokyo (JP)

( * ) Notice: Subject to any disclaimer, the term of this patent is extended or adjusted under 35 U.S.C. 154(b) by 0 days.

(21) Appl. No.: 15/916,502

(22) Filed: Mar. 9, 2018

(65) Prior Publication Data

US 2018/0194061 A1 Jul. 12, 2018

Related U.S. Application Data

(63) Continuation of application No. PCT/JP2016/076189, filed on Sep. 6, 2016.

(30) Foreign Application Priority Data

Sep. 11, 2015 (JP) ................. 2015-179954

(51) Int. Cl.
| | |
|---|---|
| *B33Y 10/00* | (2015.01) |
| *B29C 64/40* | (2017.01) |
| *A61L 27/00* | (2006.01) |
| *B33Y 30/00* | (2015.01) |
| *B29C 39/00* | (2006.01) |
| *B29C 64/118* | (2017.01) |
| *A61L 27/18* | (2006.01) |
| *A61L 27/22* | (2006.01) |
| *A61L 27/26* | (2006.01) |
| *C08L 71/08* | (2006.01) |
| *C12N 5/00* | (2006.01) |

(52) U.S. Cl.
CPC .............. *B33Y 10/00* (2014.12); *A61L 27/00* (2013.01); *A61L 27/18* (2013.01); *A61L 27/222* (2013.01); *A61L 27/26* (2013.01); *B29C 39/00* (2013.01); *B29C 64/118* (2017.08); *B29C 64/40* (2017.08); *B33Y 30/00* (2014.12); *C08L 71/08* (2013.01); *C12N 5/0018* (2013.01); *C08L 2203/02* (2013.01); *C12N 2513/00* (2013.01)

(58) Field of Classification Search
CPC ....... B29C 64/118; B29C 64/40; B29C 39/00; A61L 27/18; A61L 27/222; A61L 27/26; A61L 27/00; C12N 5/0018; C12N 2513/00; C08L 71/08; C08L 2203/02; B33Y 30/00; B33Y 10/00
See application file for complete search history.

(56) References Cited

U.S. PATENT DOCUMENTS

| | | | |
|---|---|---|---|
| 6,992,172 | B1 | 1/2006 | Chang et al. |
| 7,438,860 | B2 | 10/2008 | Takagi et al. |
| 2004/0256973 | A1* | 12/2004 | Imamura ............... B05B 5/0533 313/483 |
| 2005/0008497 | A1 | 1/2005 | Takagi et al. |
| 2010/0062531 | A1 | 3/2010 | De Boer et al. |
| 2010/0075902 | A1 | 3/2010 | De Boer et al. |
| 2010/0105618 | A1 | 4/2010 | De Boer et al. |
| 2010/0119574 | A1 | 5/2010 | De Boer et al. |
| 2012/0089238 | A1 | 4/2012 | Kang et al. |
| 2012/0101040 | A1 | 4/2012 | Ogiwara et al. |
| 2012/0107372 | A1 | 5/2012 | De Boer et al. |
| 2013/0066045 | A1 | 3/2013 | Bellan et al. |
| 2013/0071441 | A1 | 3/2013 | Iwazawa et al. |

(Continued)

FOREIGN PATENT DOCUMENTS

| | | |
|---|---|---|
| CN | 1572498 A | 2/2005 |
| CN | 1908775 A | 2/2007 |

(Continued)

OTHER PUBLICATIONS

Stachowiak, AN et al. Bioactive hydrogels with an ordered cellular structure combine interconnected macroporosity and robust mechanical properties. Advanced Materials. 2005. 17(4): 399-403. (Year: 2005).*
Communication dated May 8, 2019, from the State Intellectual Property Office of People's Republic of China in counterpart Application No. 201680052293.5.
International Search Report in Application No. PCT/JP2016/076189 dated Nov. 29, 2016.
Written Opinion in Application No. PCT/JP2016/076189 dated Nov. 29, 2016.
International Preliminary Report on Patentability dated Mar. 13, 2018, issued in International Application No. PCT/JP2016/076189.
Communication dated Oct. 4, 2018 from the European Patent Office in counterpart Application No. 16844350.5.
Communication dated Jul. 16, 2019, from the Korean Intellectual Property Office in application No. 10-2018-7004982.

(Continued)

*Primary Examiner* — Susan E. Fernandez
(74) *Attorney, Agent, or Firm* — Sughrue Mion, PLLC

(57) ABSTRACT

A method for producing a gelatin structure, the method including forming a three-dimensional structure having a hollow part using gelatin as a material, is provided, and a gelatin structure production system is provided. A biocompatible material structure having a three-dimensional structure is formed by jetting a liquid obtained by melting a biocompatible material that is solid at normal temperature and is water-soluble and thermoplastic, through a nozzle unit; and stacking the biocompatible material on a liquid landing surface of a substrate. The surface of the biocompatible material structure is coated with a coating film containing gelatin, gelatin is attached to the periphery of the biocompatible material structure to form a gelatin structure, the gelatin structure is shaped, the biocompatible material structure is dissolved, and the shape of the biocompatible material structure is transferred to the interior of the gelatin structure. For the formation of the biocompatible material structure, a first biocompatible material, or a third biocompatible material obtained by mixing a second biocompatible material with the first biocompatible material, is used.

16 Claims, 24 Drawing Sheets

(56) References Cited

U.S. PATENT DOCUMENTS

2014/0094590 A1    4/2014   Ogiwara
2015/0202344 A1    7/2015   Iwazawa et al.

FOREIGN PATENT DOCUMENTS

| | | |
|---|---|---|
| EP | 1014176 A2 | 6/2000 |
| JP | 2002511284 A | 4/2002 |
| JP | 2008194968 A | 8/2008 |
| JP | 2010518833 A | 6/2010 |
| JP | 2010519251 A | 6/2010 |
| JP | 2010519252 A | 6/2010 |
| JP | 2010519293 A | 6/2010 |
| JP | 2012206995 A | 10/2012 |
| JP | 2014012114 A | 1/2014 |
| JP | 2014151524 A | 8/2014 |
| JP | 6143438 B2 | 6/2017 |
| KR | 1020130037324 A | 4/2013 |
| WO | 2004085473 A2 | 10/2004 |
| WO | 2008103041 A1 | 8/2008 |
| WO | 2010128672 A1 | 11/2010 |
| WO | 2010147109 A1 | 12/2010 |
| WO | 2012133610 A1 | 10/2012 |
| WO | 2015/069619 A1 | 5/2015 |

\* cited by examiner

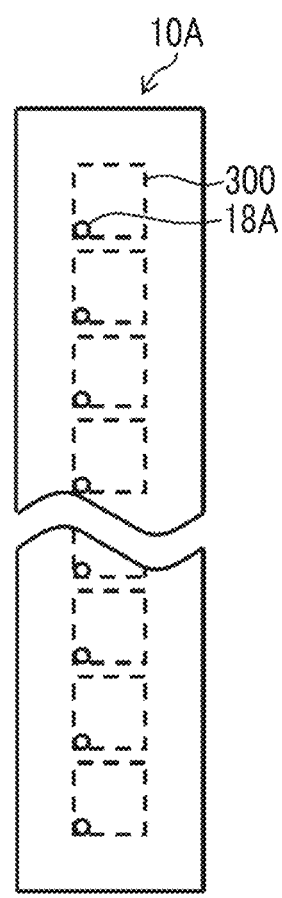

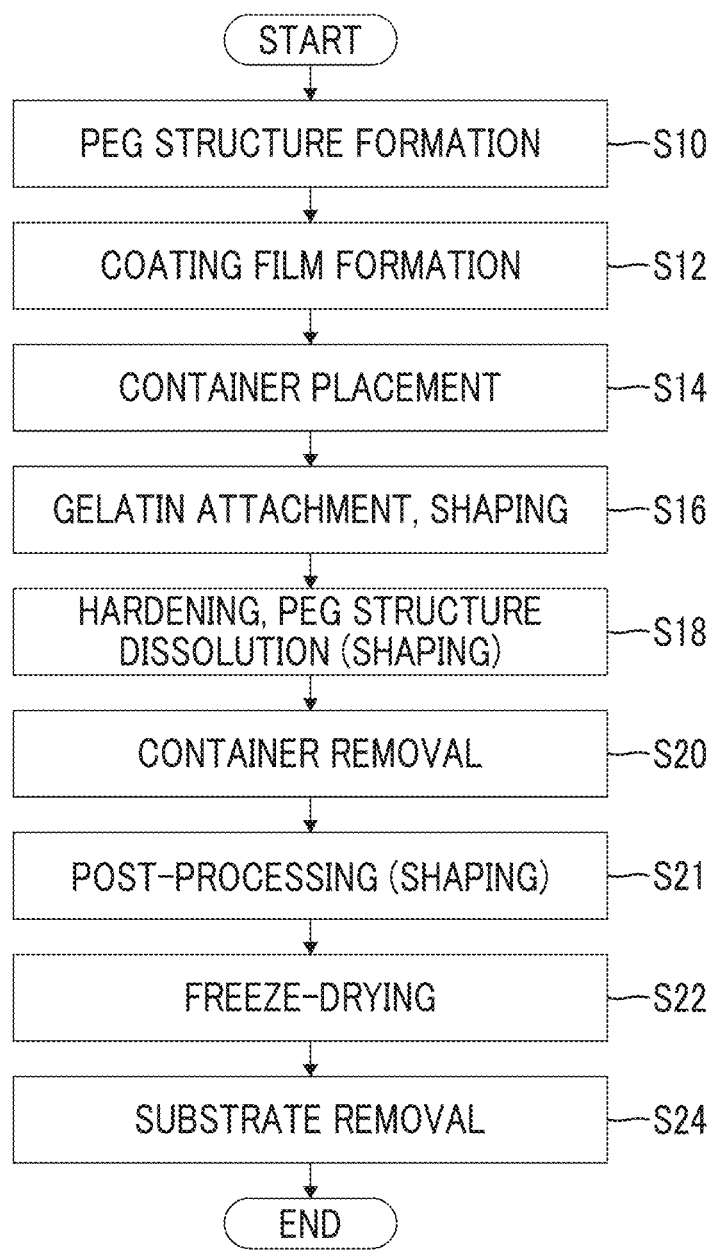

METHOD FOR PRODUCING GELATIN STRUCTURE, AND GELATIN STRUCTURE PRODUCTION SYSTEM

CROSS-REFERENCE TO RELATED APPLICATIONS

The present application is a Continuation of PCT International Application No. PCT/JP2016/076189 filed on Sep. 6, 2016 claiming priority under 35 U.S.C § 119(a) to Japanese Patent Application No. 2015-179954 filed on Sep. 11, 2015. Each of the above applications is hereby expressly incorporated by reference, in their entirety, into the present application.

BACKGROUND OF THE INVENTION

1. Field of the Invention

The present invention relates to a method for producing a gelatin structure, and a gelatin structure production system. More particularly, the invention relates to the formation of a gelatin structure using gelatin that does not allow easy maintenance of shape in a case in which a three-dimensional structure is produced.

2. Description of the Related Art

For the purpose of regeneration medicine, development of three-dimensional cell culture technologies using biocompatible materials is in progress. Many of these are beginning to be materialized by utilizing 3D printing technologies that have developed rapidly since 1990's.

The description "3D printer" means a three-dimensional printer. Hereinafter, in the present specification, a three-dimensional printer will be described as 3D printer.

Gelatin and collagen are materials effective as scaffold materials for cells. Particularly, for the gelatin produced by gene recombination as described in JP2012-206995A or WO2012/133610A1, clinical experiments of embedding the gelatin in the body of a patient have been initiated.

JP2014-151524A describes a method for producing a three-dimensional structure that can be utilized in scaffolds, which serve as scaffolding for cells, and the like, the three-dimensional structure including a hollow part having an arbitrary three-dimensional shape.

The method for producing a three-dimensional structure described in JP2014-151524A uses gelatin and a so-called temperature-sensitive polymer, which is a material that changes into a solid or a liquid depending on temperature, and a three-dimensional structure is formed by directly performing patterning three-dimensionally by an electrostatic inkjet method.

In the method for producing a three-dimensional structure described in JP2014-151524A, gelatin is utilized in dummy members that are finally removed. Under low temperature conditions in which the shape of gelatin can be maintained, gelatin as a dummy member is embedded in a temperature-sensitive polymer, subsequently the temperature is adjusted to a temperature that is higher than or equal to the melting point of gelatin and lower than or equal to the melting point of the temperature-sensitive polymer, and thereby a three-dimensional structure of the temperature-sensitive polymer having a hollow part, from which only gelatin has been removed, is formed.

The term dummy member as used in the present specification corresponds to the term dummy part in JP2014-151524A.

JP1994-143438A (JP-H06-143438A) describes a three-dimensional structure producing apparatus that utilizes, in a case in which a three-dimensional structure is formed using an ultraviolet-curable adhesive, polyethylene glycol, which is a water-soluble resin, as a support.

In the three-dimensional structure producing apparatus described in JP1994-143438A (JP-H06-143438A), a photocurable adhesive is jetted out, the photocurable adhesive is cured by irradiating the adhesive with light for curing, a mold of a three-dimensional structure having a desired shape is formed by alternately repeating jetting and curing, and the mold is filled with a resin. Thus, a three-dimensional structure having a desired shape is formed.

That is, the three-dimensional structure producing apparatus described in JP1994-143438A (JP-H06-143438A) irradiates an ultraviolet-curable adhesive in various layers with ultraviolet in a spotted manner, cures the ultraviolet-curable adhesive, and forms a mold for a three-dimensional structure.

Independently of the formation of a mold for a three-dimensional structure, and in parallel to the formation of a mold for a three-dimensional structure, formation of a support part that supports the external side of the three-dimensional structure using polyethylene glycol is carried out.

JP1994-143438A (JP-H06-143438A) describes that after a three-dimensional structure is obtained, the polyethylene glycol as a support part can be removed by a solvent such as water.

Meanwhile, the term three-dimensional structure according to the present specification corresponds to the term three-dimensional object according to JP1994-143438A (JP-H06-143438A).

JP2002-511284A describes a method for producing a three-dimensional structure that is supplied to a living test subject. In the method for producing a three-dimensional structure described in JP2002-511284A, a three-dimensional structure is formed by fused deposition modeling, which is currently a general 3D printing method, by combining a non-water-soluble silicone resin with gelatin or the like.

Fused deposition modeling is a method in which one layer is formed by a method of melting a molding material such as a resin by heat, drawing the molding material into a mold of a shape cross-section of a single layer portion, and solidifying the molding material; a method of injecting a thread-like molding material through a fine nozzle; and a method of jetting out liquid droplets of a molding material through a nozzle in the same manner as in an inkjet method, concavities and convexities of the surface are shaped, and a subsequent layer is similarly drawn and solidified on the one layer.

Fused deposition modeling requires a support part; however, it has been devised that a material different from the molding material is molded as the material of the support part, and then only the support part is dissolved. Fused deposition modeling may be referred to as fused lamination modeling or FDM. FDM is an abbreviation for fused deposition modeling.

The terms nozzle and three-dimensional structure according to the present specification correspond to the terms nozzle and three-dimensional texture according to JP2002-511284A.

JP2008-194968A describes a direct molding method for a polymer material and a direct molding apparatus. In the direct molding method for a polymer material described in JP2008-194968A, a three-dimensional structure of a thermoplastic resin having biocompatibility is formed by fused deposition molding by using a pressing type dispenser.

Meanwhile, the term thermoplastic resin according to the present specification corresponds to the term thermoplastic polymer material according to JP2008-194968A.

SUMMARY OF THE INVENTION

However, in regard to the formation of a gelatin structure that is excellent as a cell scaffold, it is difficult to maintain the shape of gelatin itself alone, and a practical process for the formation of a gelatin structure is not established.

Furthermore, in regard to the formation of a gelatin structure using a dummy member, in a case in which a non-water-soluble material is used as the dummy member, it is difficult to check whether the dummy member will be completely removed, and it cannot be said that the gelatin structure can reliably cope with being embedded in the body.

The method for producing a three-dimensional structure as described in JP2014-151524A discloses a technology for forming a three-dimensional structure using a temperature-sensitive polymer, in which gelatin is used for a dummy member, and JP2014-151524A is not intended to disclose a technology for forming a three-dimensional structure using gelatin.

In the three-dimensional structure producing apparatus described in JP1994-143438A (JP-H06-143438A), polyethylene glycol is used as a material for forming a support part that supports the external side of a mold for a three-dimensional structure. The support part formed from polyethylene glycol is formed by repeating jetting and cooling of polyethylene glycol.

Meanwhile, JP1994-143438A (JP-H06-143438A) has no specific disclosure on general conditions such as the conditions for jetting of polyethylene glycol.

JP2002-511284A does not describe a specific method for removing the silicone resin. Furthermore, in the method for producing a three-dimensional structure as described in JP2002-511284A, in a case in which a water-soluble material is utilized as a dummy member, it is expected that the structure of the dummy member cannot be maintained because the dummy member is dissolved by the water of gelatin.

In regard to the method for direct molding of a polymer material as described in JP2008-194968A, since a filament-like thermoplastic polymer is used, the method is effective for materials having relatively high melting points. However, a material that undergoes significant fluctuations in viscosity depending on temperature and thereby easily liquefies, such as polyethylene glycol, is inappropriate to be applied to the method.

The present invention was achieved in view of such circumstances, and it is an object of the invention to provide a method for producing a gelatin structure, by which a three-dimensional structure having a hollow part is formed by using gelatin as a material, and to provide a gelatin structure production system.

In order to achieve the object described above, the following aspects of the invention are provided.

A method for producing a gelatin structure according to a first aspect is a method comprising: a biocompatible material structure forming step of jetting a liquid obtained by melting a biocompatible material that is solid at normal temperature, the biocompatible material being water-soluble and thermoplastic, into a droplet state through a nozzle unit, stacking the biocompatible material on a liquid landing surface, which is a surface of a substrate where liquid droplets land, and forming a biocompatible material structure having a three-dimensional structure formed from the biocompatible material; a coating film forming step of forming a coating film containing gelatin, which coats the surface of the biocompatible material structure formed in the biocompatible material structure forming step; a gelatin structure forming step of attaching gelatin to the periphery of the biocompatible material structure having the surface coated with the coating film formed in the coating film forming step, and thereby forming a gelatin structure; a shaping step of shaping the gelatin structure formed in the gelatin structure forming step into a predetermined shape; and a dissolving step of dissolving at least a portion of the biocompatible material structure by utilizing the water on the biocompatible material structure, and transferring a shape of the biocompatible material structure to an interior of the gelatin structure, wherein in the biocompatible material structure forming step, the biocompatible material structure is formed using a first biocompatible material having a molecular weight distribution that can be adjusted to a viscosity range enabling jetting of the material alone in a temperature range in which the temperature of the biocompatible material jetted out through the nozzle unit can be adjusted, the first biocompatible material having a viscosity of from 100 milliPascal·second to 5,000 milliPascal·second, or a third biocompatible material obtained by mixing the first biocompatible material with a second biocompatible material having a molecular weight distribution that cannot be adjusted to a viscosity range enabling jetting of the material alone in a temperature range in which the temperature of the biocompatible material jetted out through the nozzle unit can be adjusted, the third biocompatible material having a viscosity of from 100 milliPascal·second to 10,000 milliPascal·second.

According to the first aspect, a gelatin structure having a three-dimensional structure that uses gelatin, for which maintenance of a three-dimensional shape is difficult, the gelatin structure having the shape of the biocompatible material structure transferred to the interior, can be formed.

Furthermore, by delaying dissolution of the biocompatible material structure by means of a coating film, the biocompatible material structure does not dissolve until gelatin hardens, and the biocompatible material structure can be caused to remain.

The biocompatible material according to the present invention is a material capable of forming a three-dimensional structure at normal temperature, and is a material that is melted and liquefied by adjusting the temperature to a temperature of from 60° C. to 130° C.

For the shaping in the shaping step, an aspect of introducing gelatin in a liquid state into a container, hardening the gelatin, and transferring the shape of the container can be applied. As another aspect of the shaping step, an aspect of post-processing solid gelatin that has been hardened may be mentioned.

According to a second aspect, the biocompatible material structure forming step in the method for producing a gelatin structure of the first aspect can be configured such that a biocompatible material structure is formed using a first biocompatible material including polyethylene glycol, or a second biocompatible material including polyethylene glycol.

According to the second aspect, polyethylene glycol can be applied as the biocompatible material.

According to a third aspect, the biocompatible material structure forming step in the method for producing a gelatin structure of the first aspect or the second aspect can be configured such that the biocompatible material structure is formed using a biocompatible material including a polyethylene glycol having a molecular weight distribution of more than 2,700 and less than 3,300, a polyethylene glycol having a molecular weight distribution of more than 5,500 and less than 6,500, or a polyethylene glycol having a molecular weight distribution of more than 8,800 and less than 11,200, as the first biocompatible material.

According to the third aspect, formation of a biocompatible material structure using the first biocompatible material, which is a kind of biocompatible material that meets the jettability conditions for being capable of jetting out through a nozzle unit and also meets the laminatability conditions for being capable of laminating at normal temperature, is possible.

According to a fourth aspect, the biocompatible material structure forming step in the method for producing a gelatin structure according to any one of the first aspect to the third aspect can be configured such that a biocompatible material structure is formed by applying a polyethylene glycol having a molecular weight distribution of more than 15,000 and less than 25,000 as the second biocompatible material, applying a polyethylene glycol having a molecular weight distribution of more than 2,700 and less than 3,300, a polyethylene glycol having a molecular weight distribution of more than 5,500 and less than 6,500, or a polyethylene glycol having a molecular weight distribution of more than 8,800 and less than 11,200 as the first biocompatible material, and using a third biocompatible material obtained by incorporating at least any one polyethylene glycol of a polyethylene glycol having a molecular weight distribution of more than 2,700 and less than 3,300, a polyethylene glycol having a molecular weight distribution of more than 5,500 and less than 6,500, and a polyethylene glycol having a molecular weight distribution of more than 8,800 and less than 11,200, into the first biocompatible material at a proportion of from 20% by mass to 80% by mass.

According to the fourth aspect, a biocompatible material structure can be formed using a third biocompatible material that meets the jettability conditions for being capable of jetting through a nozzle unit and meets the laminatability conditions for being capable of laminating at normal temperature, by mixing the first biocompatible material with the second biocompatible material.

According to a fifth aspect, the biocompatible material structure forming step in the method for producing a gelatin structure according to any one of the first aspect to the fourth aspect can be configured such that a biocompatible material structure having an inclined portion that is inclined with respect to a liquid landing surface is formed by moving the nozzle unit and the substrate relative to each other to a direction of a line normal to the liquid landing surface, which is the surface of the substrate where liquid droplets land, and by moving the nozzle unit and the substrate relative to each other within a plane parallel to the liquid landing surface.

According to the fifth aspect, a biocompatible material structure having an inclined portion that is inclined with respect to the liquid landing surface of a substrate can be formed.

According to a sixth aspect, the biocompatible material structure forming step in the method for producing a gelatin structure of the fifth aspect can be configured such that an inclined portion lies along a direction having an angle of 60 degrees or more with respect to the liquid landing surface is formed using a first biocompatible material having a viscosity of from 4,000 milliPascal·second to 5,000 milliPascal·second, or a third biocompatible material having a viscosity of from 500 milliPascal·second to 10,000 milliPascal·second.

According to the sixth aspect, an inclined portion lying along a direction having an angle of 60 degrees or more with respect to the liquid landing surface can be formed by adjusting the viscosity of the first biocompatible material or the third biocompatible material.

According to a seventh aspect, the biocompatible material structure forming step in the method for producing a gelatin structure of the fifth aspect or the sixth aspect can be configured such that an inclined portion lying along a direction having an angle of 30 degrees or more and less than 60 degrees with respect to the liquid landing surface, is formed using a third biocompatible material having a viscosity of from 2,000 milliPascal·second to 10,000 milliPascal·second.

According to the seventh aspect, an inclined portion lying along a direction having an angle of 30 degrees or more and less than 60 degrees with respect to the liquid landing surface can be formed by adjusting the viscosity of the third biocompatible material.

According to an eighth aspect, the biocompatible material structure forming step in the method for producing a gelatin structure according to any one of the fifth aspect to the seventh aspect can be configured such that a biocompatible material structure having a vertical part lying along the direction of a line normal to the liquid landing surface can be formed by moving the nozzle unit and the substrate relative to each other in the direction of a line normal to the liquid landing surface of the substrate.

According to the eighth aspect, a biocompatible material structure having a vertical part lying along the direction of a line normal to the liquid landing surface of the substrate can be formed.

According to a ninth aspect, the biocompatible material structure forming step in the method for producing a gelatin structure of the eighth aspect can be configured such that a biocompatible material structure having a horizontal part lying along a direction orthogonally intersecting the direction of formation of the vertical part is formed by moving the nozzle unit and the substrate relative to each other in the direction orthogonally intersecting the direction of formation of the vertical part.

According to the ninth aspect, a biocompatible material structure having a horizontal part lying along a direction orthogonally intersecting the direction of formation of the vertical part can be formed.

A biocompatible material structure having a vertical part and a horizontal part in combination can be formed by combining the method for producing a gelatin structure according to the eighth aspect and the method for producing a gelatin structure according to the ninth aspect.

According to a tenth aspect, the biocompatible material structure forming step in the method for producing a gelatin structure according to any one of the first aspect to the ninth aspect can be configured such that a biocompatible material structure is formed using the first biocompatible material having a viscosity of from 100 milliPascal·second to 5,000 milliPascal·second in the temperature range of from 60° C. to 130° C.

According to the tenth aspect, the viscosity of the first biocompatible material can be adjusted to a value of from 100 milliPascal·second to 5,000 milliPascal·second by adjusting the temperature to a value of from 60° C. to 130° C.

According to an eleventh aspect, the biocompatible material structure forming step in the method for producing a gelatin structure according to any one of the first aspect to the tenth aspect can be configured such that a biocompatible material structure is formed using the third biocompatible material having a viscosity of from 100 milliPascal·second to 10,000 milliPascal·second in the temperature range of from 100° C. to 130° C.

According to the eleventh aspect, the viscosity of the third biocompatible material can be adjusted to a value of from 100 milliPascal·second to 10,000 milliPascal·second by adjusting the temperature to a value of from 100° C. to 130° C.

According to a twelfth aspect, the biocompatible material structure forming step in the method for producing a gelatin structure according to any one of the first aspect to the eleventh aspect can be configured such that a biocompatible material structure is formed by stacking a biocompatible material in the liquid droplet state on the substrate having the liquid landing surface that is hydrophilic for the biocompatible material.

According to the twelfth aspect, collapsing or folding of the biocompatible material structure is prevented.

According to a thirteenth aspect, the biocompatible material structure forming step in the method for producing a gelatin structure according to any one of the first aspect to the twelfth aspect can be configured such that a biocompatible material structure is formed by stacking a biocompatible material in the liquid droplet state on the substrate having the liquid landing surface that is hydrophobic for the biocompatible material.

According to the thirteenth aspect, detachment of the biocompatible material structure from the substrate is facilitated.

According to a fourteenth aspect, the method for producing a gelatin structure according to any one of the first aspect to the thirteenth aspect can be configured to include a drying step of eliminating at least a portion of the water contained in the gelatin structure.

According to the fourteenth aspect, the gelatin structure can be insolubilized by drying by eliminating the water in the gelatin structure.

An aspect of the fourteenth aspect may be an aspect in which the gelatin structure is subjected to a drying cooling treatment.

According to a fifteenth aspect, the coating film forming step in the method for producing a gelatin structure according to any one of the first aspect to the fourteenth aspect can be configured to include particulate gelatin spraying step of spraying particulate gelatin on the surface of the biocompatible material structure, and a humidifying step of humidifying the biocompatible material structure having particulate gelatin sprayed on the surface, by applying the conditions of a temperature range and a humidity range in which at least a portion of the biocompatible material structure dissolves, the conditions being conditions of a temperature range and a humidity range in which at least a portion of the particulate gelatin dissolves.

According to the fifteenth aspect, a coating film is formed by melting particulate gelatin, and thereby the coating film and the gelatin structure can be integrated.

According to a sixteenth aspect, the dissolving step in the method for producing a gelatin structure according to any one of the first aspect to the fifteenth aspect can be configured such that the biocompatible material structure is subjected to the action of water originating from gelatin, thereby at least a portion of the biocompatible material structure is dissolved, and thereby the shape of the biocompatible material structure is transferred to the interior of the gelatin structure.

According to the sixteenth aspect, the biocompatible material structure can be dissolved by water originating from gelatin.

According to a seventeenth aspect, the method for producing a gelatin structure according to any one of the first aspect to the sixteenth aspect can be configured such that gelatin is natural gelatin or recombinant peptide.

According to the seventeenth aspect, production of a gelatin structure using natural gelatin that is easily available, or production of a recombinant peptide gelatin structure having excellent non-infectiousness is enabled.

According to an eighteenth aspect, there is provided a gelatin structure production system, comprising: a biocompatible material structure forming unit of jetting a liquid obtained by melting a biocompatible material that is solid at normal temperature, the biocompatible material being water-soluble and thermoplastic, into a droplet state through a nozzle unit, stacking the biocompatible material on a liquid landing surface, which is a surface of a substrate where liquid droplets land, and forming a biocompatible material structure having a three-dimensional structure formed from the biocompatible material; a coating film forming unit of forming a coating film containing gelatin, which coats the surface of the biocompatible material structure formed by the biocompatible material structure forming unit; a gelatin structure forming unit of attaching gelatin to the periphery of the biocompatible material structure having the surface coated with the coating film formed by the coating film forming unit, and thereby forming a gelatin structure; a shaping unit of shaping the gelatin structure formed by the gelatin structure forming unit into a predetermined shape; and a dissolving unit of dissolving at least a portion of the biocompatible material structure by subjecting the biocompatible material structure to the action of water, and transferring a shape of the biocompatible material structure to an interior of the gelatin structure, in which the biocompatible material structure forming unit forms a biocompatible material structure using a first biocompatible material having a molecular weight distribution that can be adjusted to a viscosity range enabling jetting of the material alone in a temperature range in which the temperature of the biocompatible material jetted out through the nozzle unit can be adjusted, the first biocompatible material having a viscosity of from 100 milliPascal·second to 5,000 milliPascal·second, or a third biocompatible material obtained by mixing the first biocompatible material with a second biocompatible material having a molecular weight distribution that cannot be adjusted to obtain a viscosity range enabling jetting of the material alone in a temperature range in which the temperature of the biocompatible material jetted out through the nozzle unit can be adjusted, the third biocompatible material having a viscosity of from 100 milliPascal·second to 10,000 milliPascal·second.

According to the nineteenth aspect, an effect similar to that of the first aspect can be obtained.

According to the eighteenth aspect, matters similar to the matters specified in the second aspect to the seventeenth aspect can be combined as appropriate. In that case, the process or treatment specified in connection with the method for producing a gelatin structure can be understood as an element of means that is responsible for a treatment or function corresponding to the process or treatment.

According to the present invention, a gelatin structure having a three-dimensional structure using gelatin, for which maintenance of a three-dimensional shape is difficult, the gelatin structure having the shape of a biocompatible material structure transferred to the interior, can be formed. Furthermore, by delaying dissolution of the biocompatible material structure by means of a coating film, the biocompatible material structure does not dissolve until gelatin hardens, and the biocompatible material structure can be caused to remain.

BRIEF DESCRIPTION OF THE DRAWINGS

FIG. 11A is a plan view showing a disposition of nozzle units of a liquid jetting head.

FIG. 14 is a flowchart illustrating the order of another aspect of the method for producing a gelatin structure.

DESCRIPTION OF THE PREFERRED EMBODIMENTS

Hereinafter, preferred embodiments of the present invention will be explained in detail with reference to the attached drawings.

[Overview of Method for Producing Gelatin Structure]

Figure 1A:
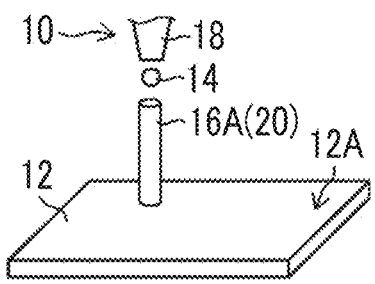
FIG. 1A is a schematic diagram illustrating the formation of a polyethylene glycol structure.

FIG. 1A to FIG. 1I are schematic diagrams illustrating an outline of a method for producing a gelatin structure. FIG. 1A is a schematic diagram illustrating the formation of a polyethylene glycol structure. PEG is a term representing polyethylene glycol.

In the formation of a PEG structure illustrated in FIG. 1A, PEG liquid droplets 14 in droplet state are jetted out from a jet dispenser 10 toward a liquid landing surface 12A of a substrate 12, and a PEG structure 20 is formed. In FIG. 1A, a vertical PEG pillar 16A is depicted as the PEG structure 20.

As illustrated in FIG. 1A, the jet dispenser 10 includes a nozzle unit 18 that ejects PEG in a droplet state.

The PEG applied to the formation of the vertical PEG pillar 16A is solid at normal temperature and has thermoplastic properties. In regard to the PEG applied to the formation of the vertical PEG pillar 16A, the temperature adjustment range or the temperature setting range of the heating apparatus includes temperatures higher than the melting point of the PEG.

For the PEG applied to the formation of the vertical PEG pillar 16A, the temperature is adjusted by a heating apparatus capable of adjusting the temperature to a value of from 60° C. to 130° C., the PEG is brought to a liquid state at the time of being jetted through the nozzle unit 18 of the jet dispenser 10, and the viscosity of the PEG is adjusted to a viscosity range enabling jetting of the PEG from the jet dispenser 10. Normal temperature in the method for producing a gelatin structure according to the present embodiment can be adjusted to, for example, a value of from 5° C. to 35° C. Temperature adjustment by a heating apparatus can be carried out in a temperature adjusting step of adjusting the temperature of the PEG jetted through the nozzle unit.

Figure 1B:
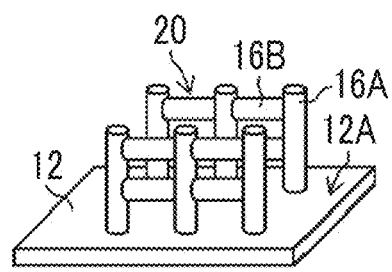
FIG. 1B is a perspective view illustrating an example of the polyethylene glycol structure.

FIG. 1B is a perspective view illustrating an example of the polyethylene glycol structure. FIG. 1B illustrates a PEG structure 20 formed on a liquid landing surface 12A of a substrate 12. The PEG structure 20 illustrated in FIG. 1B has a structure combining a plurality of vertical PEG pillars 16A and a plurality of horizontal PEG pillars 16B. The vertical PEG pillars 16A correspond to a vertical part. The horizontal PEG pillars 16B correspond to a horizontal part.

The vertical PEG pillars 16A illustrated in FIG. 1B are formed by stacking PEG liquid droplets 14 along the direction of a line normal to the liquid landing surface 12A of the substrate 12. The horizontal PEG pillars 16B illustrated in FIG. 1B are formed along a direction parallel to the liquid landing surface 12A of the substrate 12, the direction orthogonally intersecting the direction of formation of the vertical PEG pillars 16A.

The term parallel according to the present specification includes substantial parallelism, by which two directions intersect; however, an operating effect identical to that of parallelism is provided. Furthermore, the term orthogonal intersection according to the present specification includes substantial orthogonal intersection by which, in a case in which two directions intersect at an angle of more than 90 degrees, or in a case in which two directions intersect at an angle of less than 90 degrees, an operating effect identical to that in the case in which two directions intersect at 90 degrees is provided.

Furthermore, the term identicalness according to the present specification includes substantial identicalness, by which although there are differences in the configurations as objects; however, an operating effect identical to that of identicalness can be obtained.

Figure 1C:
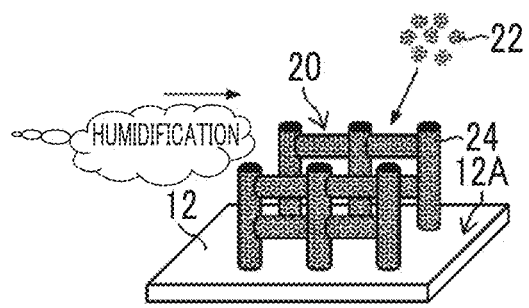
FIG. 1C is a schematic diagram illustrating the formation of a coating film.
Figure 1D:
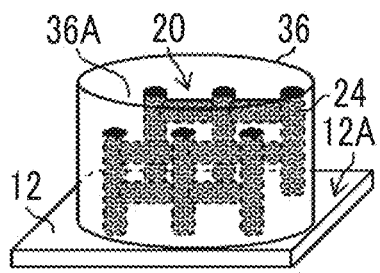
FIG. 1D is a schematic diagram illustrating the attachment of gelatin.
Figure 1E:
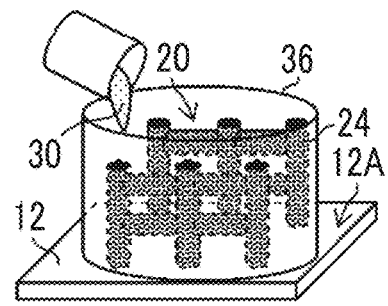
FIG. 1E is a schematic diagram illustrating the attachment of gelatin.
Figure 1F:
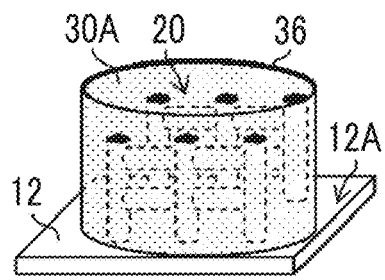
FIG. 1F is a schematic diagram illustrating hardening and dissolution.
Figure 1G:
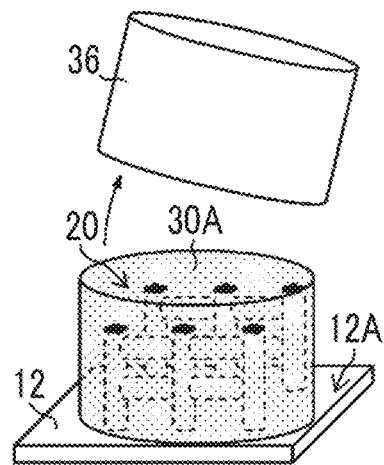
FIG. 1G is a schematic diagram illustrating removal of the container.
Figure 1H:
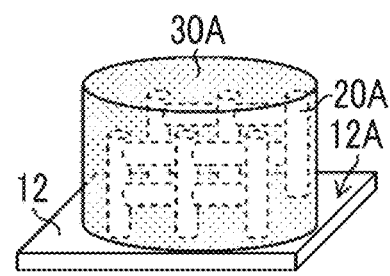
FIG. 1H is a schematic diagram illustrating solid gelatin.
Figure 1I:
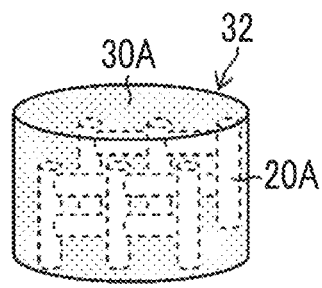
FIG. 1I is a schematic diagram illustrating a gelatin structure.

The PEG structure 20 illustrated in FIG. 1B has a shape corresponding to the three-dimensional shape of the hollow part of the gelatin structure assigned with reference numeral 32 and depicted in FIG. 1I. The hollow part is assigned with reference numeral 20A and is depicted in FIG. 1I.

FIG. 1B illustrates a PEG structure 20 having vertical PEG pillars 16A and also having horizontal PEG pillars 16B; however, a PEG structure 20 having only vertical PEG pillars 16A, or a PEG structure 20 having only horizontal PEG pillars 16B may also be formed. Furthermore, PEG pillars in an inclined direction formed along a direction that intersects the vertical PEG pillars 16A or horizontal PEG pillars 16B.

That is, the three-dimensional shape of the PEG structure 20 can be determined in accordance with the three-dimensional shape of the hollow part of the gelatin structure.

Figure 2:
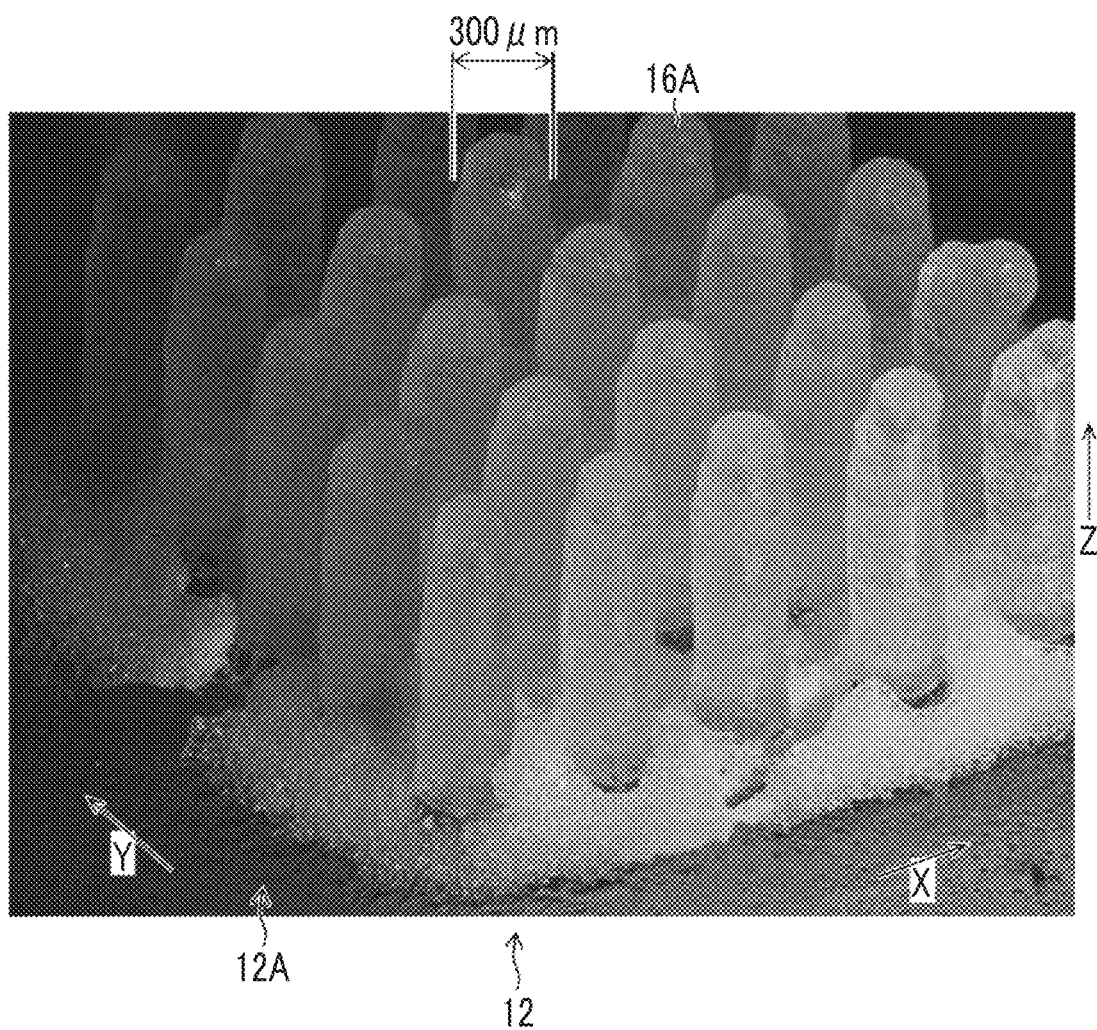
FIG. 2 is an explanatory diagram for polyethylene glycol pillars.

FIG. 2 is an explanatory diagram illustrating polyethylene glycol pillars. Hereinafter, the same reference numerals will be assigned to configurations identical to the configurations explained previously, and further description will not be repeated as appropriate.

In FIG. 2, a plurality of vertical PEG pillars 16A, which have been shown in FIG. 1B, are formed. A plurality of the vertical PEG pillars 16A shown in FIG. 2 are disposed at an interval of disposition determined in advance along the X-direction and the Y-direction.

First, the positions of the jet dispenser 10 and the substrate 12 illustrated in FIG. 1A in the X-direction and the Y-direction are determined. Next, the PEG liquid droplets 14 illustrated in FIG. 1A are jetted out through the jet dispenser 10.

The jet dispenser 10 and the substrate 12 is moved a plurality of times relative to each other in the Z-direction, and jetting is performed a plurality of times. As a result, a plurality of PEG liquid droplets 14 are laminated along the Z-direction, a plurality of the PEG liquid droplets 14 coalesce and harden, and thereby a vertical PEG pillar 16A having a cylindrical shape as shown in FIG. 2 is formed.

The X-direction is an aspect of the direction parallel to the liquid landing surface of the substrate. The Y-direction is another aspect of the direction parallel to the liquid landing surface of the substrate. The Z-direction corresponds to the direction of a line normal to the liquid landing surface of the substrate.

PEG is solid at normal temperature, and the PEG liquid droplets 14 harden immediately after landing on the liquid landing surface 12A of the substrate 12. Furthermore, as a PEG liquid droplet 14 lands and hardens on the liquid landing surface 12A of the substrate 12, and a subsequently jetted PEG liquid droplet 14 lands thereon, the PEG liquid droplet 14 that has landed on the PEG liquid droplet 14 hardens immediately.

In this manner, a plurality of PEG liquid droplets 14 are laminated in sequence, and thereby a vertical PEG pillar 16A that stands along the Z-direction is formed.

In a case in which a vertical PEG pillar 16A is formed at an arbitrary landing position, the jet dispenser 10 and the substrate 12 illustrated in FIG. 1A are moved relative to each other, thereby the position of landing of PEG liquid droplets 14 on the liquid landing surface 12A of the substrate 12 is changed, a plurality of PEG liquid droplets 14 are laminated in sequence along the Z-direction at the changed position of landing, and thus a vertical PEG pillar 16A is formed.

In this manner, relative movement of the jet dispenser 10 and the substrate 12 in the X-direction, the Y-direction, and the Z-direction, and lamination of a plurality of PEG liquid droplets 14 are repeated sequentially, and thereby a plurality of vertical PEG pillars 16A as shown in FIG. 2 are formed. The relative movement of the jet dispenser 10 and the substrate 12 has the same meaning as the relative movement of the nozzle unit 18 and the substrate 12.

The diameter of the vertical PEG pillar 16A shown in FIG. 2 is 300 micrometers. Here, the diameter of the vertical PEG pillar 16A can be determined based on the jetting volume of the PEG liquid droplet 14 and the wettability of the liquid landing surface 12A of the substrate 12. In a case in which the wettability of the liquid landing surface 12A of the substrate 12 is uniform, the diameter of the vertical PEG pillar 16A can be regulated by regulating the jetting volume of the PEG liquid droplets 14. The term micro- is a prefixed unit representing $10^{-6}$. The diameter of the vertical PEG pillar 16A has the same meaning as the width of the vertical PEG pillar 16A.

A plurality of the vertical PEG pillars 16A shown in FIG. 2 are such that the intervals of disposition in the X-direction and the Y-direction are equal; however, the intervals of disposition in the X-direction and the Y-direction can be individually set as appropriate.

The horizontal PEG pillars 16B illustrated in FIG. 1B can be formed by changing the posture of the substrate 12 on which the vertical PEG pillars 16A have been formed, arranging the liquid landing surface 12A to be parallel to the Z-direction, and carrying out the same procedure as that for the vertical PEG pillars 16A.

That is, the horizontal PEG pillars 16B are formed by moving the jet dispenser 10 and the substrate 12 relative to each other in a direction orthogonally intersecting the direction of formation of the vertical PEG pillars 16A, and laminating PEG liquid droplets 14 along the direction orthogonally intersecting the direction of formation of the vertical PEG pillars 16A.

By alternately repeating the formation of vertical PEG pillars 16A and the formation of horizontal PEG pillars 16B, a PEG structure 20 composed of a plurality of vertical PEG pillars 16A and a plurality of horizontal PEG pillars 16B as illustrated in FIG. 1B can be formed.

The diameter of the horizontal PEG pillars 16B can be determined based on the jetting volume of the PEG liquid droplets 14 and the wettability of the vertical PEG pillars 16A. In a case in which the wettability of the vertical PEG pillars 16A is uniform, the diameter of the horizontal PEG pillars 16B can be regulated by regulating the jetting volume of the PEG liquid droplets 14. The diameter of the horizontal PEG pillar 16B has the same meaning as the width of the horizontal PEG pillar 16B.

According to the present specification, in a case in which it is not necessary to distinguish vertical PEG pillars 16A from horizontal PEG pillars 16B, the pillars will be described as PEG pillars 16.

FIG. 1C is a schematic diagram illustrating the formation of a coating film. The formation of a coating film illustrated in FIG. 1C includes a first humidifying step, in which a humidity range to the extent that dissolution of the PEG structure 20 will not proceed is set as the humidity conditions, and the surface of the PEG structure 20 is brought to a state of being covered with minute water droplets. An example of the humidity conditions to the extent that dissolution of the PEG structure 20 does not proceed may be humidity conditions in which in a case in which the diameter of the PEG structure 20 is 200 micrometers, and the length of the PEG structure 20 is 1 millimeter, the relative humidity at 25° C. is set to 90%, and the duration of humidification is set to 1 minute.

The formation of the coating film illustrated in FIG. 1C includes a microparticulate gelatin spraying step of spraying microparticulate gelatin 22 over the periphery of the PEG structure 20 and attaching the microparticulate gelatin thereto. An example of the microparticulate gelatin 22 may be an example having an average diameter of 50 micrometers, obtained by micronizing fish gelatin using a micronizing apparatus such as a bead mill. The average diameter of the microparticulate gelatin 22 can be changed as appropriate according to the shape and size of the PEG pillar 16.

Here, the diameter of the microparticulate gelatin 22 is a diameter obtainable by regarding the shape of the microparticulate gelatin 22 as a sphere and determining the diameter of the sphere from the volume of the microparticulate gelatin 22. Furthermore, the average diameter of the microparticulate gelatin 22 is an average value of the diameters of a plurality of microparticulate gelatin 22 particles included in a unit volume.

Regarding the average diameter of the microparticulate gelatin 22, the setting value for the micronizing apparatus may be applied. The microparticulate gelatin 22 is an aspect of particulate gelatin.

The formation of a coating film as illustrated in FIG. 1C includes a second humidifying step, in which a portion of the microparticulate gelatin 22 attached to the surface of the PEG structure 20 is dissolved by humidification, and thereby a coating film 24 is formed on the periphery of the PEG structure 20. Regarding the humidity conditions for the second humidifying step, the same humidity conditions as those for the first humidifying step can be applied.

Although it is not depicted in the diagram, the formation of a coating film includes a pressure reduction step of leaving the PEG structure 20 having a coating film 24 formed on the periphery, in an environment with reduced pressure, and accelerating drying of the coating film 24. In a case in which acceleration of drying of the coating film 24 is unnecessary, the pressure reduction step can be omitted.

The first humidifying step and the second humidifying step can be carried out as a humidifying step, without distinguish the two, in a case in which the humidity conditions are the same. That is, the formation of the coating film illustrated in FIG. 1C can be carried out as a step of performing humidification under humidity conditions that have been set up in advance, attaching microparticulate gelatin 22 to the surface of the PEG structure 20, further continuing humidification, and thereby forming a coating film of gelatin on the periphery of the PEG structure 20.

In the formation of a coating film as illustrated in FIG. 1C, a coating film having a desired thickness can be formed by repeating a first humidifying step, a microparticulate gelatin spraying step, and a second humidifying step a plurality of times. For example, in a case in which attachment of microparticulate gelatin having an average diameter of 50 micrometers is performed once, a coating film having a thickness of 100 micrometers is formed. In a case in which the first humidifying step, the microparticulate gelatin attaching step, and the second humidifying step are carried out two times, a coating film having a thickness of 200 micrometers is formed. The thickness of the coating film can be measured using an electron microscope.

The PEG structure 20 having the coating film 24 formed on the periphery as illustrated in FIG. 1C is an aspect of the PEG structure 20 and is an aspect of a biocompatible material structure. Hereinafter, it is considered that the PEG structure 20 includes a PEG structure 20 having a coating film 24 formed thereon, and the PEG structure 20 having the coating film 24 formed thereon may be described as the PEG structure 20.

FIG. 1D and FIG. 1E are schematic diagrams illustrating gelatin attachment. As illustrated in FIG. 1D, the entire PEG structure 20 is covered with a container 36. The container 36 has a shape corresponding to the external shape of the gelatin structure, which is a final formed product. The gelatin structure as the final formed product is illustrated in FIG. 1I, while being assigned with reference numeral 32.

The container 36 illustrated in FIG. 1D has a size in which the entirety of the PEG structure 20 can be accommodated, and the container 36 has an opening 36A inside, through which inflow of a gelatin solution is enabled. The container 36 may be configured such that the substrate 12 and the container 36 are integrated. Regarding the material of the container 36, a resin can be applied.

As the PEG structure 20 is covered by the container 36, as illustrated in FIG. 1E, a gelatin solution 30 is poured into the container 36 through the opening 36A of the container 36. An example of the gelatin solution 30 may be a gelatin solution in which the percentage content of fish gelatin is 12 percent by mass. Fish gelatin is gelatin derived from fish. In the present embodiment, fish gelatin having a melting temperature of 23° C. is applied.

FIG. 1F is a schematic diagram illustrating hardening and dissolution. In the hardening and dissolution illustrated in FIG. 1F, the gelatin solution 30 in the container 36 can be solidified into a gel form by performing cooling under the temperature conditions that have been set in advance. An example of the cooling temperature conditions may be 4° C.

Another example of the cooling temperature may be 15° C. It was confirmed that in a case in which a gelatin solution having a concentration of 25 percent by mass at a temperature of 25° C. is introduced into a cubic container, which measures 1 centimeter on each side, and the gelatin solution is air-cooled in an environment at 15° C., the gelatin solution 30 hardens. In a case in which the concentration of the gelatin solution 30 is 20 percent by mass, it was confirmed that the gelatin solution 30 is hardened by cooling for 10 minutes. In a case in which the concentration of the gelatin solution 30 is 25 percent by mass, it was confirmed that the gelatin solution 30 is hardened by cooling for 2 minutes.

In the hardening and dissolution illustrated in FIG. 1F, the water of the gelatin solution 30 acts on the coating film 24 illustrated in FIG. 1C, and the water causes gradual integration of the coating film 24 and the gelatin solution 30. Furthermore, in the hardening and dissolution illustrated in FIG. 1F, the water of the coating film 24 and the gelatin solution 30 exert action on the PEG structure 20, and the PEG structure 20 is gradually dissolved.

That is, in the hardening and dissolution as illustrated in FIG. 1F, hardening of the gelatin solution 30 and dissolution of the PEG structure 20 proceed in parallel.

Solid gelatin represents gelatin obtained by solidifying at least a portion of a gelatin solution to the extent that the shape can be maintained even if the container 36 is removed. It is preferable that the solid gelatin is a product obtained by solidifying the entirety of a gelatin solution.

Hardening of the gelatin solution 30 also functions as a part of the shaping step of shaping solid gelatin 30A into an external shape corresponding to the shape of the container 36.

As the gelatin solution 30 in the container 36 is solidified as a result of the hardening and dissolution as illustrated in FIG. 1F, and then solid gelatin 30A is obtained, the container 36 covering the solid gelatin 30A is removed, as illustrated in FIG. 1G. Removal of the container as illustrated in FIG. 1G is a part of the shaping step of shaping the solid gelatin 30A into an external shape corresponding to the shape of the container 36.

In a case in which the PEG structure 20 dissolves during the hardening and dissolution illustrated in FIG. 1F, a gelatin structure in which the three-dimensional shape of the PEG structure 20 has been transferred to the interior of the solid gelatin 30A is formed.

In the solid gelatin 30A illustrated in FIG. 1H, a hollow part 20A corresponding to the three-dimensional shape of the PEG structure 20 illustrated in FIG. 1B is formed. The solid gelatin 30A illustrated in FIG. 1H is subjected to a freeze-drying treatment, the substrate 12 is removed, and the gelatin structure 32 as illustrated in FIG. 1I is completed. The gelatin structure 32 illustrated in FIG. 1I is insolubilized by the freeze-drying treatment.

The gelatin structure 32 may contain solid gelatin 30A that has been subjected to a freeze-drying treatment as illustrated in FIG. 1I, as well a solid gelatin 30A that has not been subjected to a freeze-drying treatment as illustrated in FIG. 1H. In other words, the solid gelatin 30A that has been subjected to a freeze-drying treatment as illustrated in FIG. 1I is an aspect of the gelatin structure, and the solid gelatin 30A that has not been subjected to a freeze-drying treatment as illustrated in FIG. 1H is another aspect of the gelatin structure.

As an aspect of the gelatin structure forming step, an aspect including the formation of a coating film as illustrated in FIG. 1C, gelatin attachment as illustrated in FIG. 1E, and gelatin hardening as illustrated in FIG. 1F may be considered. As an aspect of the shaping step, an aspect including the placement of a container as illustrated in FIG. 1D and removal of the container as illustrated in FIG. 1G may be considered.

Furthermore, dissolution of the PEG structure 20 as illustrated in FIG. 1F is an aspect of the dissolving step.

[Explanation of Procedure for Method for Producing Gelatin Structure]

Figure 3:
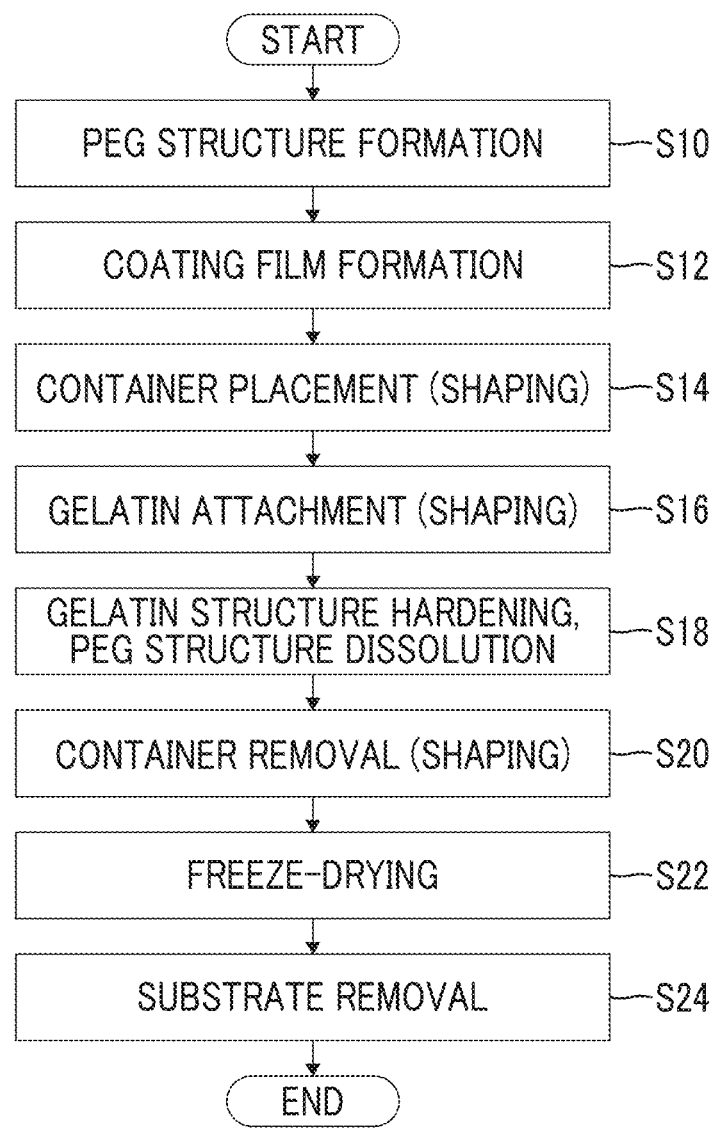
FIG. 3 is a flowchart illustrating the order of the method for producing a gelatin structure.

FIG. 3 is a flowchart showing the procedure of the method for producing a gelatin structure. In the following explanation, FIG. 1A to FIG. 1I will be referred to as appropriate.

As shown in FIG. 3, in the method for producing a gelatin structure according to the present embodiment, first, the PEG structure 20 illustrated in FIG. 1B is formed in PEG structure forming step S10. After the PEG structure 20 is formed, the process proceeds to coating film forming step S12, as shown in FIG. 3.

The PEG structure forming step S10 shown in FIG. 3 is an aspect of the biocompatible material structure forming step.

In the coating film forming step S12, a coating film 24 of gelatin is formed on the periphery of the PEG structure 20, as illustrated in FIG. 1C. After the coating film 24 of gelatin is formed on the periphery of the PEG structure 20, the process proceeds to container placement step S14, as shown in FIG. 3.

The biocompatible material structure forming step may include an aspect including the PEG structure forming step S10 shown in FIG. 3.

In the container placement step S14, as illustrated in FIG. 1D, a container 36 having a shape and structure that covers the entirety of the PEG structure 20, on which the coating film 24 of gelatin has been formed, is placed. After the container 36 is placed, the process proceeds to gelatin attaching step S16, as shown in FIG. 3.

In the gelatin attaching step S16, a gelatin solution 30 is poured into the container 36 through an opening 36A of the container 36, as illustrated in FIG. 1E. After the gelatin solution 30 is poured into the container 36, the process proceeds to hardening and dissolving step S18, as shown in FIG. 3.

In the hardening and dissolving step S18, a hardening step in which the gelatin solution 30 in the container 36 is cooled, and the solid gelatin 30A illustrated in FIG. 1F is formed; and a dissolving step in which the PEG structure 20 constructed from PEG having water-solubility is subjected to the action of water and is thereby dissolved, are carried out in parallel.

Regarding the water that is caused to have an effect on the PEG structure 20, water originating from the solid gelatin 30A can be applied.

After the solid gelatin 30A is formed by solidifying the gelatin solution 30, the process proceeds to container removal step S20, as shown in FIG. 3. In the container removal step S20, the container 36 that covers the solid gelatin 30A is removed, as illustrated in FIG. 1G. After the container 36 illustrated in FIG. 1G is removed, the process proceeds to freeze-drying step S22, as shown in FIG. 3.

In the freeze-drying step S22, as illustrated in FIG. 1H, the solid gelatin 30A is subjected to a freeze-drying treatment, and at least a portion of water of the gelatin solution 30 is removed. After the solid gelatin 30A is insolubilized by the freeze-drying treatment, the process proceeds to substrate removal step S24, as shown in FIG. 3. The freeze-drying step S22 is an aspect of the drying step.

In the substrate removal step S24, the substrate 12 is removed from the solid gelatin 30A, and a gelatin structure 32 is completed, as illustrated in FIG. 1I. In FIG. 3, an aspect in which a solid gelatin 30A having a substrate 12 attached thereto is subjected to a freeze-drying treatment, is mentioned as an example; however, a solid gelatin 30A from which a substrate 12 has been removed may also be subjected to a freeze-drying treatment.

As an aspect of the gelatin structure forming step, an aspect including the container placement step S14, the gelatin attaching step S16, the hardening step in the hardening and dissolving step S18, the container removal step S20, and the freeze-drying step S22 as shown in FIG. 3, may be considered.

As an aspect of the shaping step, an aspect including the container placement step S14 and the container removal step S20 as shown in FIG. 3 may be considered. That is, the container placement step S14 and the container removal step S20 as shown in FIG. 3 function as constituent elements of the gelatin structure forming step and also function as constituent elements of the shaping step.

Regarding the dissolving step, an aspect including a dissolving step in the hardening and dissolving step S18 shown in FIG. 3 may be considered.

The freeze-drying treatment is an aspect of treatments for the drying step.

[Configuration of Gelatin Structure Production System]

Figure 4:
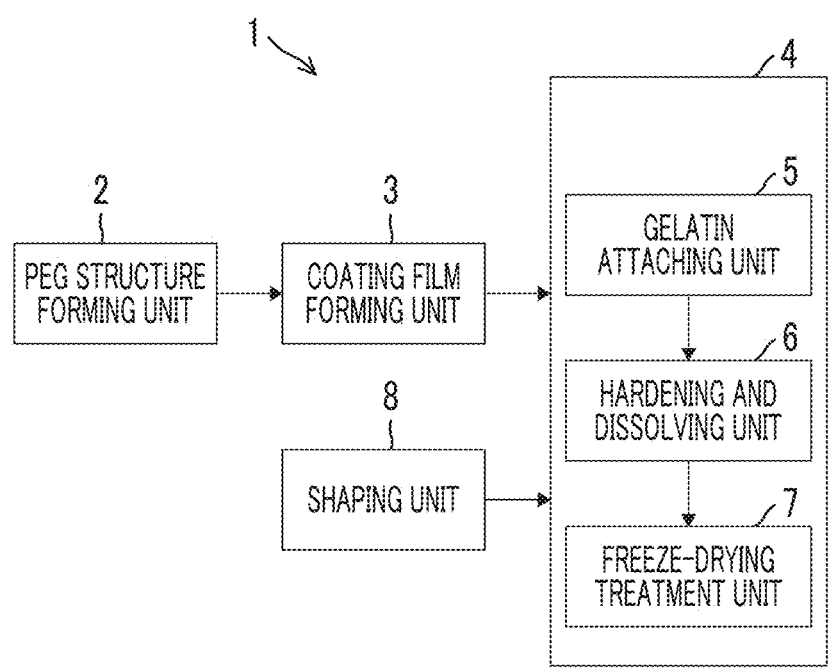
FIG. 4 is a block diagram illustrating the outline configuration of a gelatin structure production system.

FIG. 4 is a block diagram illustrating the outline configuration of a gelatin structure production system. The gelatin structure production system shown in the block diagram of FIG. 4 is a system that materializes the method for producing a gelatin structure shown in the flowchart of FIG. 3.

The gelatin structure production system 1 shown in FIG. 4 includes a PEG structure forming unit 2 for forming the PEG structure 20 illustrated in FIG. 1B; a coating film forming unit 3 for forming the coating film 24 illustrated in FIG. 1C on the periphery of the PEG structure 20 formed by the PEG structure forming unit 2; and a gelatin structure forming unit 4 for attaching gelatin to the periphery of the PEG structure 20 illustrated in FIG. 1C and thereby forming the gelatin structure 32 illustrated in FIG. 1I.

The gelatin structure forming unit 4 shown in FIG. 4 includes a gelatin attaching unit 5 for pouring a gelatin solution 30 around the PEG structure 20 illustrated in FIG. 1E; a hardening and dissolving unit 6 for cooling the gelatin solution 30 to solidify, attaching water to the PEG structure 20, and dissolving the PEG structure 20; and a freeze-drying treatment unit 7 for applying a freeze-drying treatment to the solid gelatin 30A.

Furthermore, the gelatin structure production system 1 shown in FIG. 4 includes a shaping unit 8 for shaping the solid gelatin 30A. The various units shown in FIG. 4 are distinguished only for the convenience based on the functions, and the various units can be combined or separated as appropriate.

For example, in a case in which the three-dimensional shape of the gelatin structure 32 shown in FIG. 1I, which is a final product, is determined by the shape of the container 36 shown in FIG. 1D, the shaping unit 8 shown in FIG. 3 is combined with the gelatin structure forming unit 4.

[Explanation of PEG Structure Forming Unit]

Figure 5:
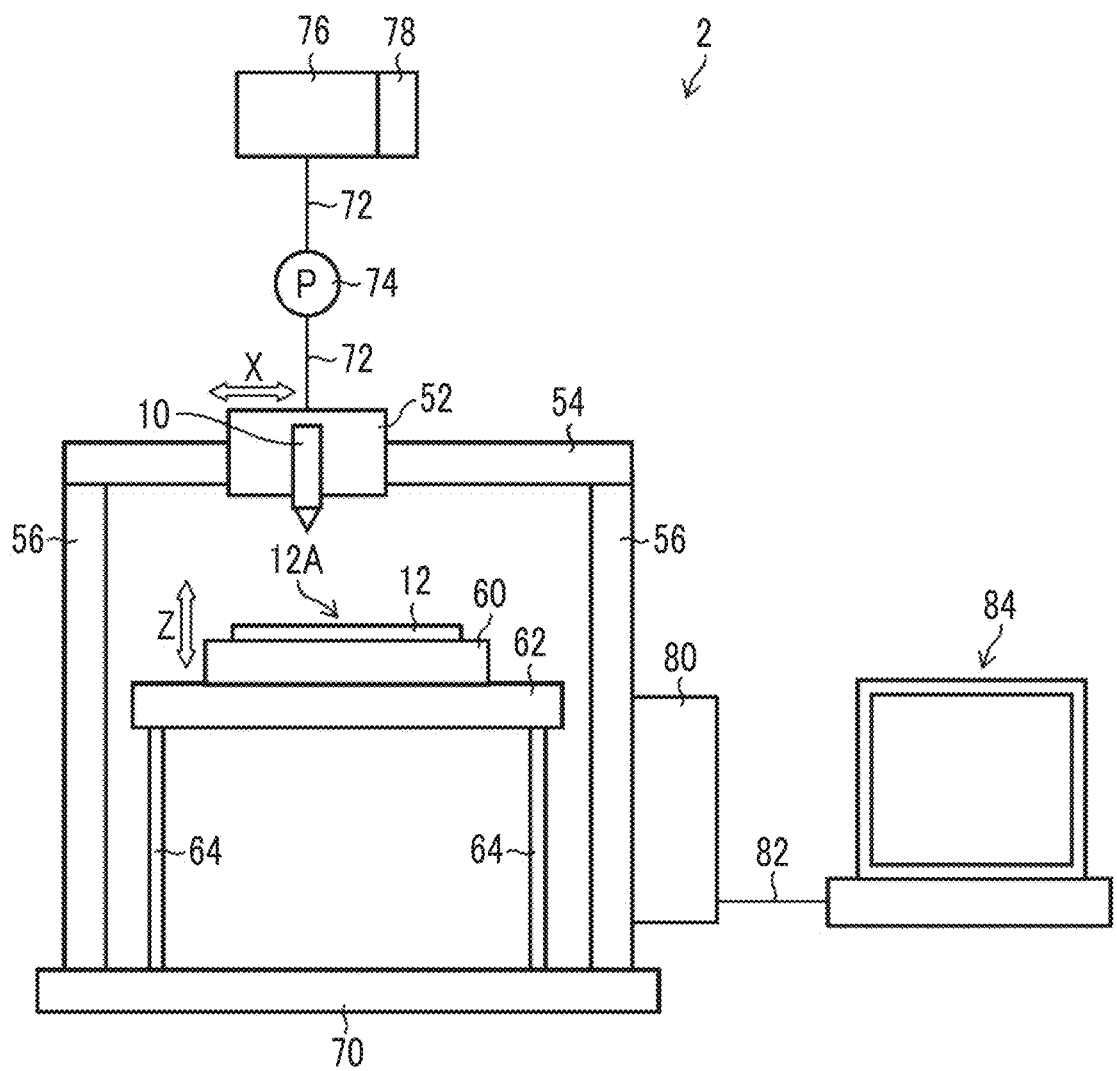
FIG. 5 is an overall configuration diagram of a polyethylene glycol structure forming unit.

Next, the PEG structure forming unit shown in FIG. 4 will be described in detail. FIG. 5 is an overall configuration diagram of a polyethylene glycol structure forming unit. The PEG structure forming unit 2 corresponds to the biocompatible material structure forming unit.

The PEG structure forming unit 2 shown in FIG. 5 forms a PEG structure on a liquid landing surface 12A of a substrate 12, by moving a jet dispenser 10 and a substrate 12 relative to each other in the X-direction, Y-direction, and Z-direction.

The PEG structure forming unit 2 includes a carriage 52 that moves the jet dispenser 10 in a reciprocating manner along the X-direction; a guide 54 that supports the carriage 52 so as to enable movement of the carriage 52 along the X-direction; and supporting pillars 56 that support two ends of the guide 54 in the X-direction.

The PEG structure forming unit 2 also includes a table 60 that supports the substrate 12, the table 60 being capable of moving along the Y-direction and the Z-direction, a support 62 that supports the table 60, and legs 64 that support the support 62. The supporting pillars 56 and the legs 64 are placed on a base platform 70.

The jet dispenser 10 is connected to a tank 76 through a flow channel 72 and a pump 74. The tank 76 accommodates PEG that is jetted out through the jet dispenser 10. The tank 76 includes a PEG temperature adjustment unit 78 that adjusts the temperature of PEG. The tank 76 accommodates liquid PEG, whose temperature has been adjusted by the PEG temperature adjustment unit 78.

The table 60 includes a Y-direction moving unit that moves a substrate supporting unit, which supports the substrate 12, along the Y-direction; and a Z-direction moving unit that moves the substrate supporting unit along the Z-direction. In FIG. 5, the substrate supporting unit, the Y-direction moving unit, and the Z-direction moving unit are not shown in the diagram. Examples of the Y-direction moving unit and the Z-direction moving unit include a linear moving mechanism and a vertical moving mechanism, which use ball screws or belts.

The PEG structure forming unit 2 includes a control unit 80 that controls the movement of the carriage 52 and the movement of the table 60 and controls the jetting of the jet dispenser 10. As illustrated in FIG. 5, the control unit 80 is connected to a personal computer 84 via a data communication line 82. The control unit 80 receives the data for the PEG structure transmitted from the personal computer 84, and executes control of the jetting of the jet dispenser 10, control of the movement of the carriage 52, and control of the movement of the table 60, based on the data for the PEG structure.

FIG. 5 illustrates an aspect of a wired connection between the control unit 80 and the personal computer 84 in the PEG structure forming unit 2; however, an aspect of implementing data communication through a wireless connection is also possible. Furthermore, an aspect of disposing the personal computer 84 shown in FIG. 5 in the outside of the installation place for the PEG structure forming unit 2 and connecting the personal computer 84 to the control unit 80 of the PEG structure forming unit 2 through a computer network.

FIG. 5 illustrates an aspect of moving the jet dispenser 10 along the X-direction and moving the substrate 12 along the Y-direction and the Z-direction; however, it is desirable, if possible, that the PEG structure forming unit 2 moves the jet dispenser 10 and the substrate 12 relative to each other in the X-direction, Y-direction, and Z-direction.

Figure 6:
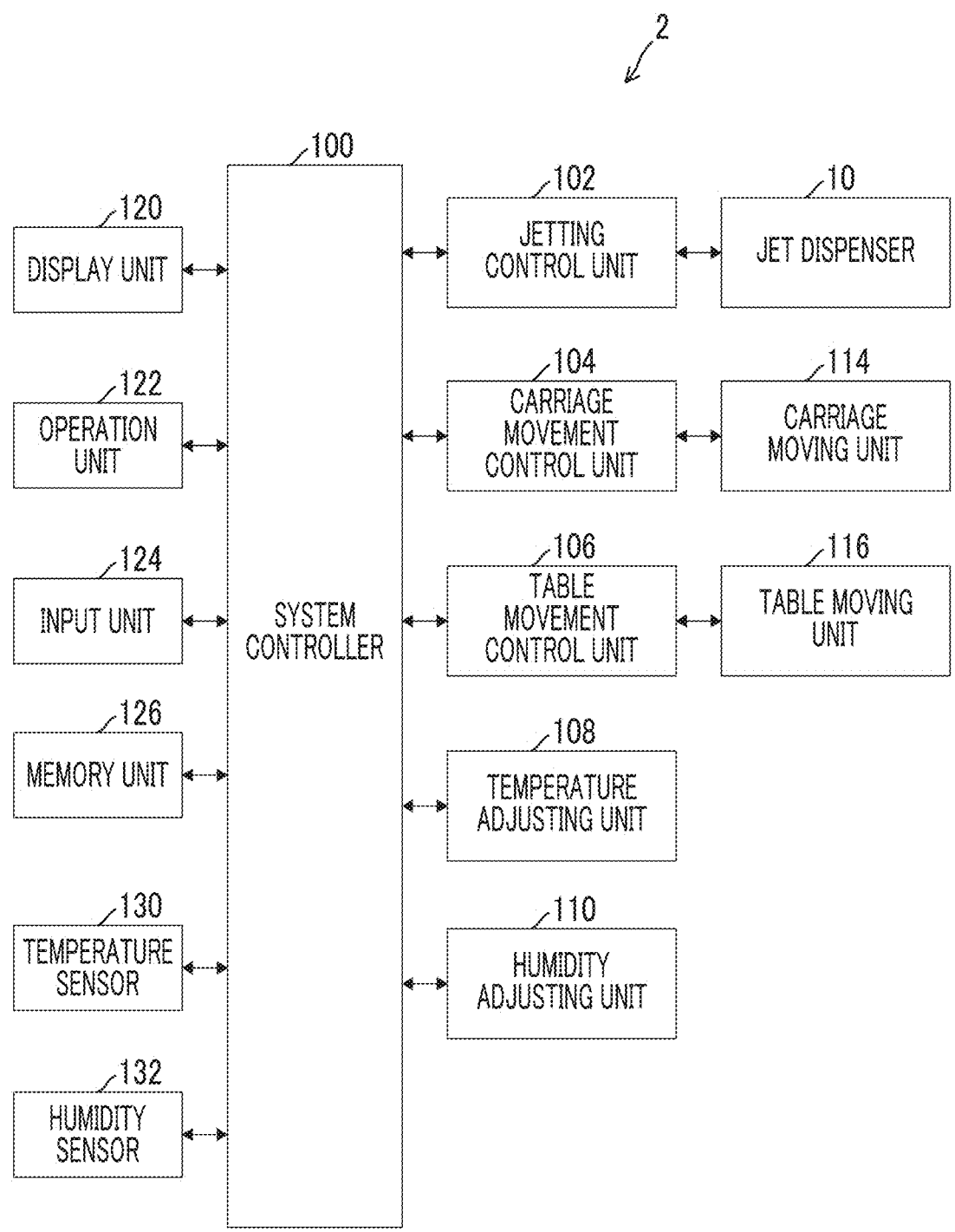
FIG. 6 is a block diagram of a control system in the polyethylene glycol structure forming unit.

FIG. 6 is a block diagram of a control system for the polyethylene glycol structure forming unit. The control system shown in FIG. 6 includes the control unit 80 shown in FIG. 5.

The PEG structure forming unit 2 includes a system controller 100 that comprehensively control the various units. The system controller 100 is composed of a central processing unit and a memory. The central processing unit includes a unit called Central Processing Unit or CPU. CPU is an abbreviation for Central Processing Unit.

The control system shown in FIG. 6 includes a jetting control unit 102, a carriage movement control unit 104, a table movement control unit 106, a temperature adjustment unit 108, and a humidity adjustment unit 110.

The jetting control unit 102 controls jetting of liquid droplets by the jet dispenser 10 based on the command signals coming from the system controller 100. The control of jetting by the jet dispenser 10 includes control of the jetting timing and control of the jetting volume.

The carriage movement control unit 104 controls the movement of the carriage moving unit 114 and control the movement of the carriage 52 shown in FIG. 5, both based on the command signals coming from the system controller 100. The carriage moving unit 114 shown in FIG. 6 includes a motor as a driving source, and a driving mechanism connected to the rotating shaft of the motor.

The table movement control unit 106 controls the movement of the table moving unit 116 and controls the movement of the table 60 shown in FIG. 5. The table moving unit 116 of FIG. 6 includes an X-direction moving mechanism that moves the substrate 12 shown in FIG. 5 in the X-direction, and a Y-direction moving mechanism that moves the substrate 12 in the Y-direction.

The temperature adjustment unit 108 is configured to include a PEG temperature adjustment unit that maintains the temperature of the PEG supplied to the jet dispenser 10 in a certain range appropriate for the jetting of PEG based on the command signals coming from the system controller 100; and an environment temperature adjustment unit that maintains the environment temperature of the jet dispenser 10 in a certain range appropriate for the jetting of PEG and the hardening of PEG. The PEG temperature adjustment unit includes the PEG temperature adjustment unit 78 shown in FIG. 5.

The humidity adjustment unit 110 maintains the environment humidity of the jet dispenser 10 in a certain range appropriate for the jetting of PEG based on the command signals coming from the system controller 100.

The control system shown in FIG. 6 includes a display unit 120, an operation unit 122, an input unit 124, and a memory unit 126.

The display unit 120 displays various kinds of information based on the command signals coming from the system controller 100. As the display unit, display devices such as a liquid crystal display device can be applied.

In the operation unit 122, an operation member such as a keyboard, a mouse, or a joystick is applied. Information inputted by means of the operation unit 122 is transmitted to various units via the system controller 100.

An aspect configured such that the display unit 120 and the operation unit 122 are integrated, while a display device of touch panel type is used, is also possible.

The input unit 124 is an input interface for various information transmitted from the outside of the system. An example of the input unit 124 may be a terminal to which the data communication line 82 shown in FIG. 5 is connected. The control system may also include a radio communication interface as the input unit 124.

The memory unit 126 include a primary memory region for data, a processing region for arithmetic processing, a storage region for system parameters, and the like. The memory unit 126 shown in FIG. 6 may be composed of a plurality of memory devices.

The control system shown in FIG. 6 stores the temperature information transmitted from a temperature sensor 130 via the system controller 100. The temperature information transmitted from the temperature sensor 130 is utilized for the control of temperature by the temperature adjustment unit 108. An example of the temperature sensor 130 may be a temperature sensor that detects the temperature of PEG in the jet dispenser 10.

The control system shown in FIG. 6 stores the humidity information transmitted from the humidity sensor 132 via the system controller 100. The humidity information transmitted from the humidity sensor 132 is utilized for the control of humidity by the humidity adjustment unit 110. An example of the humidity sensor may be a humidity sensor that detects the environment humidity of the jet dispenser 10.

In regard to the control system shown in FIG. 6, system controller 100, jetting control unit 102, carriage movement control unit 104, table movement control unit 106, temperature adjustment unit 108, and humidity adjustment unit 110 are included in the control unit 80 shown in FIG. 5. An aspect including other configurations for the control system shown in FIG. 6 in the control unit 80 is also definitely possible.

[Explanation of Coating Film Forming Unit]

Figure 7:
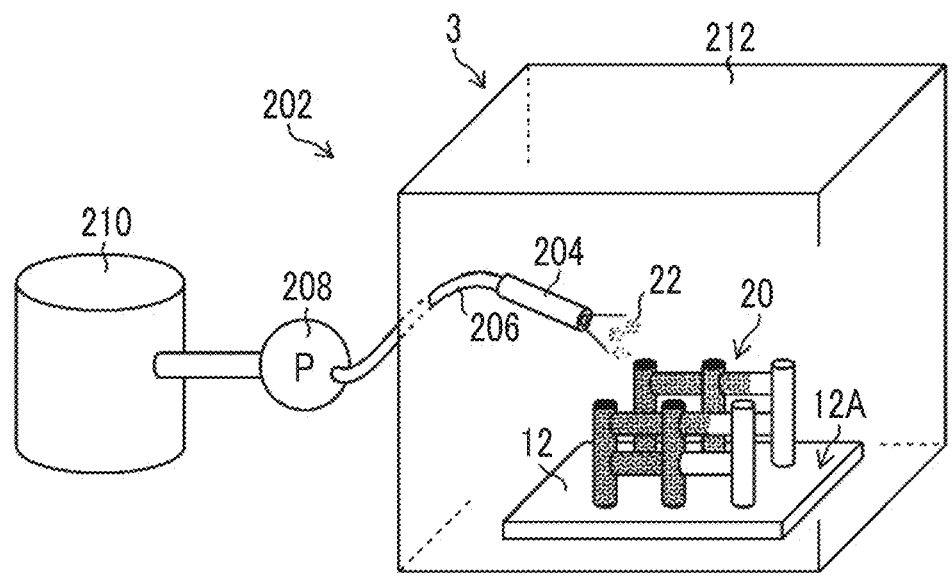
FIG. 7 is an outline configuration diagram of a coating film forming unit.

Next, the coating film forming unit 3 shown in FIG. 4 will be described in detail. FIG. 7 is an outline configuration diagram of the coating film forming unit.

The coating film forming unit 3 illustrated in FIG. 7 includes a spraying unit 202 that sprays microparticulate gelatin 22 to the PEG structure 20 formed on the substrate 12. The spraying unit 202 includes a spray nozzle unit 204, a gelatin flow channel 206, a gelatin spraying pump 208, and a gelatin tank 210.

As the gelatin spraying pump 208 is operated, microparticulate gelatin 22 is sprayed from the spray nozzle unit 204. The microparticulate gelatin 22 can be attached to the entirety of the PEG structure 20 by moving the position of the spray nozzle unit 204 using a spray nozzle moving unit that is not shown in the diagram.

The coating film forming unit 3 includes a chamber 212 that accommodates the PEG structure 20. The chamber 212 is configured such that temperature conditions can be set to the extent that dissolution of the PEG structure 20 does not proceed, and humidity conditions can be set to the extent that dissolution of the PEG structure 20 does not proceed.

Figure 8A:
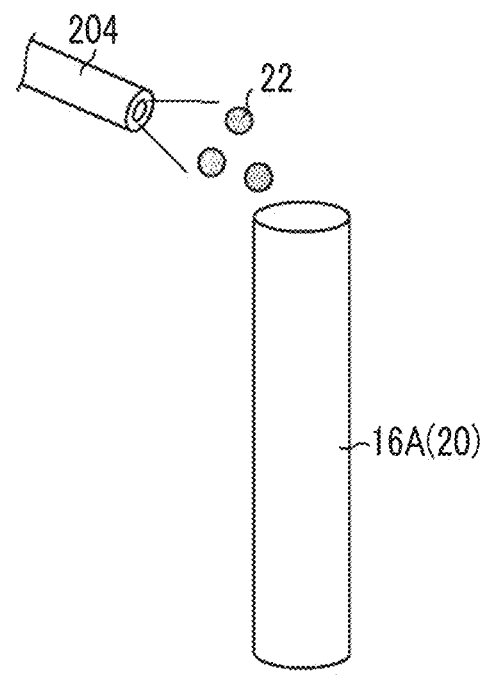
FIG. 8A is a schematic diagram of microparticulate gelatin spraying.

FIG. 8A to FIG. 8E are schematic diagrams illustrating the formation of a coating film. FIG. 8A is a schematic diagram illustrating the spraying of microparticulate gelatin. FIG. 8A illustrates a state in which microparticulate gelatin 22 is sprayed toward the polyethylene glycol structure 20, and thereby the microparticulate gelatin is attached to the PEG structure 20. In FIG. 8A, any one arbitrary vertical PEG pillar 16A among a plurality of vertical PEG pillars 16A that constitute the PEG structure 20 shown in FIG. 7 is depicted as the PEG structure 20.

In the spraying of the microparticulate gelatin shown in FIG. 8A, the PEG structure 20 is humidified under the humidity conditions including a relative humidity of 90 percent and a duration of humidification of one minute. The diameter of the vertical PEG pillar 16A shown in FIG. 8A is 200 micrometers, and the length of the vertical PEG pillar 16A shown in FIG. 8A in the direction of a line normal to the liquid landing surface 12A of the substrate 12 shown in FIG. 7 is 1 millimeter. The diameter of the vertical PEG pillar 16A has the same meaning as the width of the vertical PEG pillar 16A.

The humidity conditions disclosed herein are the same as the humidity conditions for the first humidifying step for the formation of a coating film illustrated in FIG. 1C.

Figure 8B:
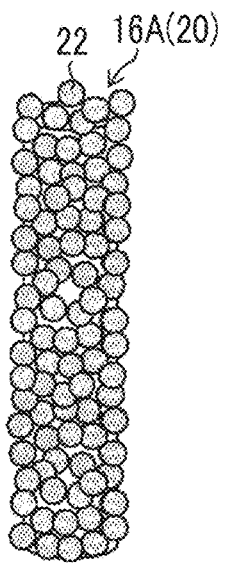
FIG. 8B is a schematic diagram of a polyethylene glycol structure having microparticulate gelatin attached over the entire surface.
Figure 8C:
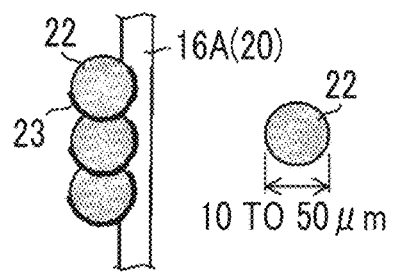
FIG. 8C is a partially magnified diagram of FIG. 8B.

FIG. 8B is a schematic diagram of a polyethylene glycol structure having microparticulate gelatin attached over the entire surface. FIG. 8C is a partially magnified diagram of FIG. 8B. As illustrated in FIG. 8C, water 23 disposed between the PEG structure 20 and the microparticulate gelatin 22 functions as an adhesive liquid and strengthens bonding between the PEG structure 20 and the microparticulate gelatin 22, while strengthening bonding between microparticulate gelatin particles 22.

In the example shown in FIG. 8C, the average diameter of the microparticulate gelatin is 50 micrometers. The diameter and the average diameter of the microparticulate gelatin are as explained previously, and no further description will be given here.

Figure 8D:
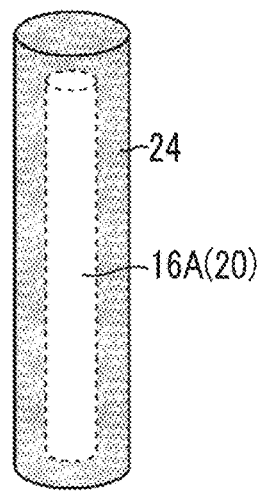
FIG. 8D is a schematic diagram of a polyethylene glycol structure having a coating film formed on the periphery.
Figure 8E:
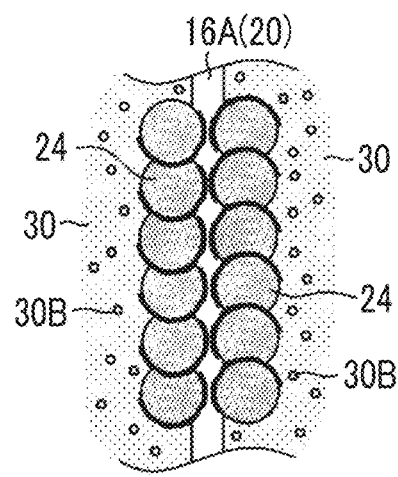
FIG. 8E is a partially magnified diagram of FIG. 8D.

FIG. 8D is a schematic diagram of a polyethylene glycol structure having a coating film formed on the periphery. FIG. 8E is a partially magnified diagram of FIG. 8D.

In a case in which humidification is continued while the humidity conditions mentioned previously as an example are applied, the humidity conditions being applied to the extent that dissolution of the PEG structure 20 does not proceed, a portion of the microparticulate gelatin 22 of the PEG structure 20 shown in FIG. 8B dissolves and coalesces with the microparticulate gelatin 22 in the surroundings, and thereby the PEG structure 20 having a coating film 24 as illustrated in FIG. 8D formed thereon is formed.

These humidity conditions are the same as the humidity conditions for the formation of a coating film as illustrated in FIG. 1C, and no further detailed description will be given here.

As illustrated in FIG. 8E, the coating film 24 suppresses migration of water molecules 30B in the gelatin solution 30 shown in FIG. 1E. Then, the progress of dissolution of the PEG structure 20 can be delayed, and the PEG structure 20 can be prevented from being dissolved, until the gelatin solution 30 hardens and becomes solid gelatin 30A.

Figure 9:
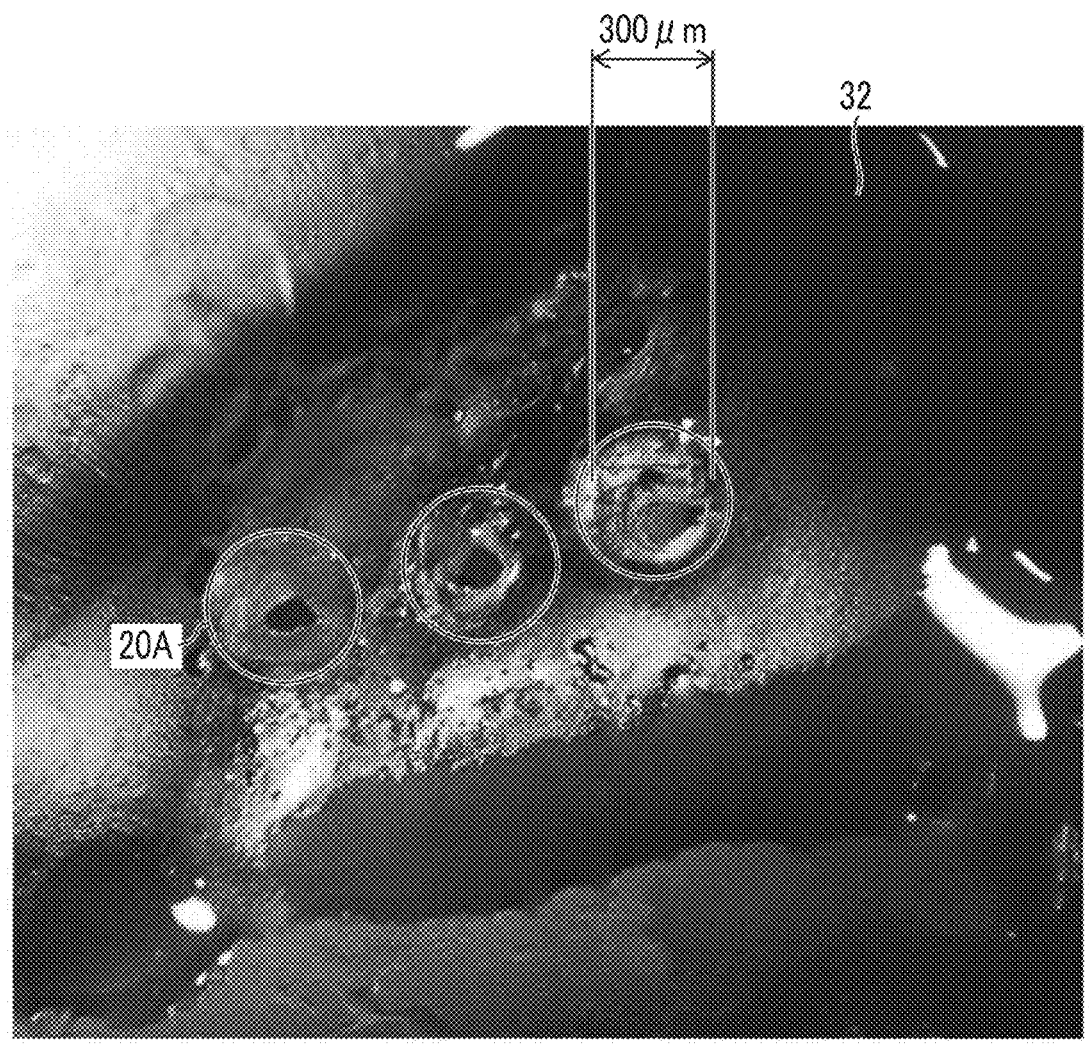
FIG. 9 is a magnified diagram of a gelatin structure after a hardening and dissolving step.

FIG. 9 is a magnified view of the gelatin structure obtainable after the hardening and dissolving step. FIG. 9 is an electron microscopic photograph showing a partially magnified view of the gelatin structure 32 shown in FIG. 1I. As shown in FIG. 9, in the interior of the gelatin structure 32, a hollow part 20A having a shape corresponding to the three-dimensional shape of the PEG structure 20 shown in FIG. 1B is formed. The diameter of the hollow part 20A shown in FIG. 9 is 300 micrometers, and this is the same as the diameter of the vertical PEG pillar 16A shown in FIG. 2.

That is, in a case in which at least a portion of the PEG structure 20 illustrated in FIG. 1B is dissolved, the three-dimensional shape of the dissolved portion in the PEG structure 20 is transferred to the interior of the gelatin structure 32.

FIG. 9 shows an aspect in which the PEG structure 20 shown in FIG. 1B has been entirely dissolved; however, some of the PEG structure 20 in a trace amount to the extent that will not impair the function of the gelatin structure 32 may remain behind.

SPECIFIC EXAMPLES OF FORMATION OF COATING FILM

Specific Example 1

The thickness of the coating film 24 shown in FIG. 8D is set to 200 micrometers. The concentration of the gelatin solution 30 shown in FIG. 1E is set to 25 percent by mass, and the temperature of the gelatin solution 30 is set to 25° C. The gelatin solution 30 was air-cooled by setting the environment temperature to 15° C.

In such a case, it was confirmed that hardening of the gelatin solution 30 can be achieved without dissolving the PEG structure 20. Furthermore, it was confirmed that the three-dimensional shape of the PEG structure 20 had been transferred to the interior of the gelatin structure 32.

Specific Example 2

The thickness of the coating film 24 shown in FIG. 8D is set to 200 micrometers. The concentration of the gelatin solution 30 shown in FIG. 1E is set to 20 percent by mass, and the temperature of the gelatin solution 30 is set to 25° C. The gelatin solution 30 was air-cooled by setting the environment temperature to 15° C.

In such a case, a duration of 10 minutes was required to harden the gelatin solution 30. Similarly to Specific Example 1, it was confirmed that hardening of the gelatin solution 30 can be achieved without dissolving the PEG structure 20. It was confirmed that the three-dimensional shape of the PEG structure 20 had been transferred to the interior of the gelatin structure 32.

Comparative Example 1

A gelatin solution 30 having a concentration of 25 percent by mass and a temperature of 25° C. was attached to the PEG structure 20 shown in FIG. 1B, without forming the coating film 24 illustrated in FIG. 8D. The gelatin solution 30 was air-cooled by setting the environment temperature to 15° C.

It was confirmed that the PEG structure 20 dissolved for 10 seconds from the completion of attachment of the gelatin solution 30. Furthermore, it was confirmed that the gelatin solution 30 hardened for 2 minutes from the completion of attachment of the gelatin solution 30.

Since the PEG structure 20 was dissolved by the water included in the gelatin solution 30 and was mixed into the gelatin solution 30, and the gelatin solution 30 hardened, it was confirmed that an inverted shape of the three-dimensional shape of the PEG structure 20 could not be obtained in the interior of the gelatin structure 32.

Comparative Example 2

The thickness of the coating film 24 shown in FIG. 8D is set to 100 micrometers. The concentration of the gelatin solution 30 is set to 25 percent by mass, and the temperature of the gelatin solution 30 is set to 25° C. The gelatin solution 30 was air-cooled by setting the environment temperature to 15° C.

It was confirmed that the PEG structure 20 was dissolved for one minute from the completion of attachment of the gelatin solution 30. That is, it was confirmed that in a case in which the thickness of the coating film 24 was set to 100 micrometers, the resistance to moisture was not sufficient.

To summarize the findings, a coating film 24 having sufficient resistance to moisture can be formed by adjusting the thickness of the coating film 24 shown in FIG. 8D. Adjustment of the thickness of the coating film 24 can be achieved based on the concentration of the gelatin solution, the hardening conditions for the gelatin solution, and the like.

[Explanation of Other Forms of PEG Structure Forming Unit]

Figure 10:
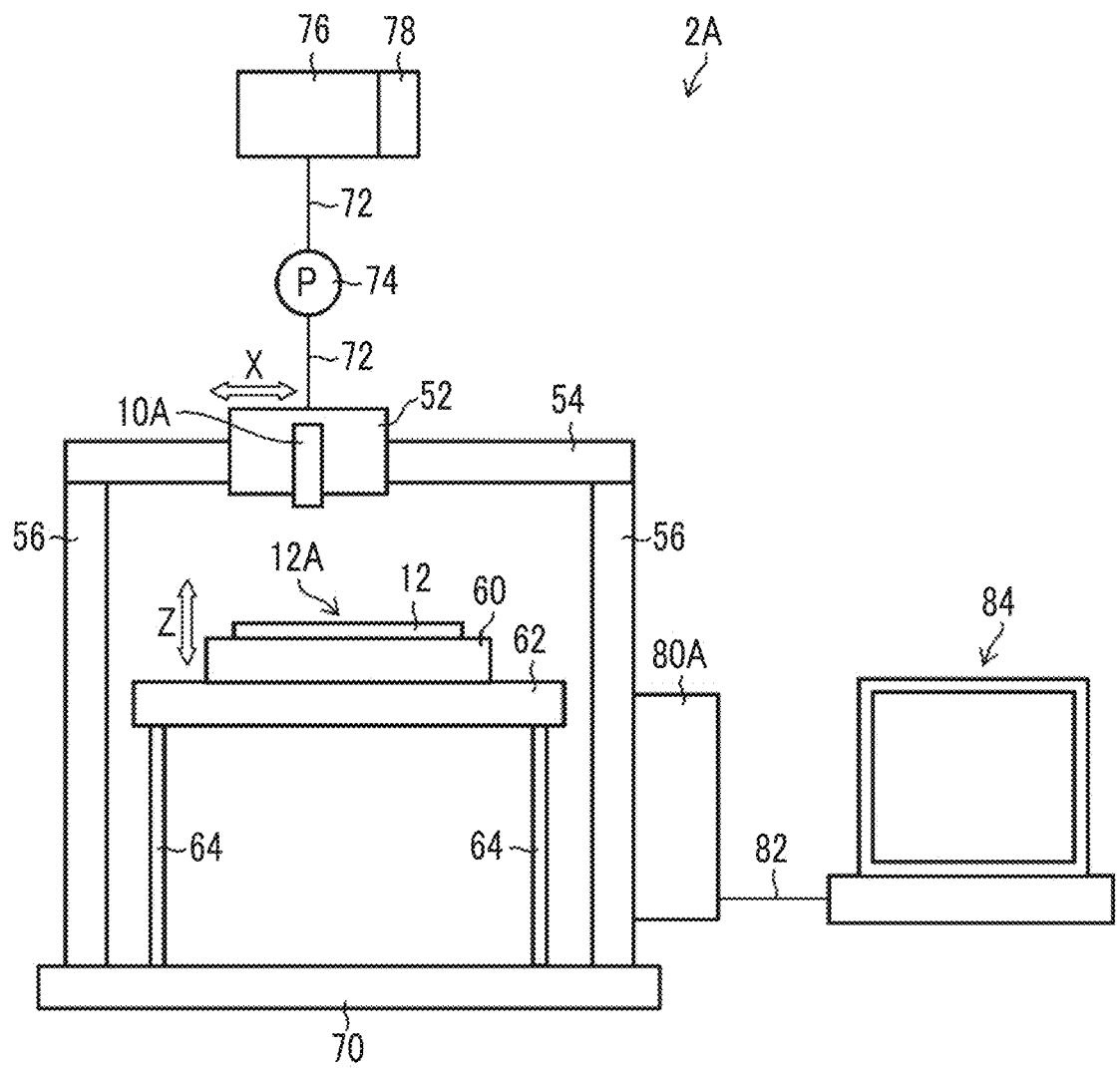
FIG. 10 is an overall configuration diagram of another embodiment of the polyethylene glycol structure forming unit.

FIG. 10 is an overall configuration diagram of another form of the polyethylene glycol structure forming unit. Here, the difference between the PEG structure forming unit 2A shown in FIG. 10 and the PEG structure forming unit 2 shown in FIG. 5 will be mainly explained, and any description of the same configurations between the PEG structure forming unit 2A shown in FIG. 10 and the PEG structure forming unit 2 shown in FIG. 5 will not be given here.

The PEG structure forming unit 2A illustrated in FIG. 10 includes a liquid jetting head 10A instead of the jet dispenser 10 of the PEG structure forming unit 2 illustrated in FIG. 5. The liquid jetting head 10A includes a plurality of nozzle units that are not shown in FIG. 10, and PEG liquid droplets 14 illustrated in FIG. 1A can be jetted out selectively from each of a plurality of the nozzle units.

The PEG structure forming unit 2A illustrated in FIG. 10 includes a control unit 80A instead of the control unit 80 of the PEG structure forming unit 2 illustrated in FIG. 5. The details of the control unit 80A will be described later.

Figure 11B:
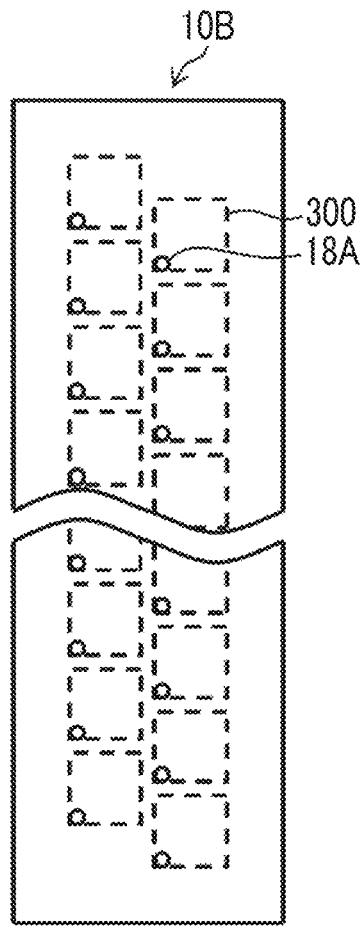
FIG. 11B is a plan view of the nozzle plane showing another disposition of nozzle units of the liquid jetting head.

FIG. 11A is a plan view of the nozzle plane showing a disposition of nozzle units of the liquid jetting head. FIG. 11B is a plan view of the nozzle plane showing another disposition of nozzle units of the liquid jetting head.

In the liquid jetting head 10A shown in FIG. 11A, a plurality of nozzle units 18A are aligned at an equal interval in one direction. Reference numeral 300 in FIG. 11A represents a pressure chamber that constitutes a part of the internal flow channel of the liquid jetting head 10A.

The liquid jetting head 10B shown in FIG. 11B has two nozzle rows in which a plurality of nozzle units 18A are aligned at an equal interval in one direction, and the positions of the nozzle units 18A in the direction of arrangement of the nozzle units 18A between one row of nozzles and the other row of nozzles are shifted from each other at a distance of ½ of the interval of nozzle disposition.

The jetting resolution in the direction of arrangement of the nozzle units of the liquid jetting head 10B shown in FIG. 11B is two times the jetting resolution in the direction of arrangement of the nozzle units of the liquid jetting head 10A shown in FIG. 11A.

The disposition of nozzle units of the liquid jetting head is not limited to the aspects shown in FIG. 11A and FIG. 11B, and it is also acceptable that a plurality of nozzle units 18A are disposed in a two-dimensional manner.

Figure 12:
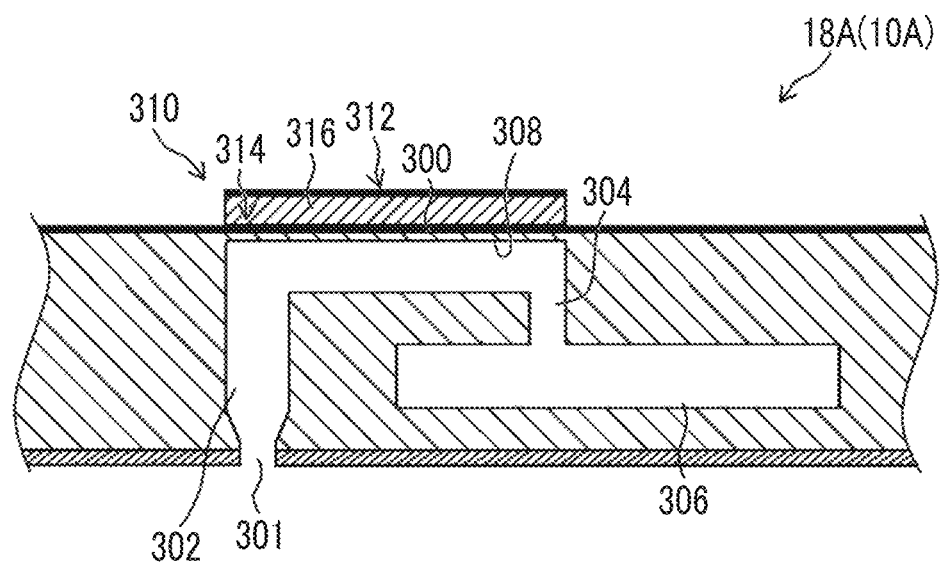
FIG. 12 is a cross-sectional view illustrating a three-dimensional configuration of the liquid jetting head.

FIG. 12 is a cross-sectional view illustrating the three-dimensional configuration of the liquid jetting head. In FIG. 12, one nozzle unit 18A among a plurality of the nozzle units 18A shown in FIG. 11A is depicted. The liquid jetting head 10A illustrated in FIG. 11A and the liquid jetting head 10B illustrated in FIG. 11B are such that the three-dimensional structure of one nozzle unit 18A is the same, and in this description, the liquid jetting head 10A shown in FIG. 11A will be explained.

As shown in FIG. 12, a nozzle opening 301 is in communication with the pressure chamber 300 through a nozzle channel 302. The pressure chamber 300 is in communication with a common flow channel 306 through a supply port 304. The ceiling face of the pressure chamber 300 has a vibrating plate 308 formed thereon. On the surface of the vibrating plate 308 on the opposite side of the pressure chamber 300, a piezoelectric element 310 is disposed.

The piezoelectric element 310 has a structure in which a piezoelectric body 316 is disposed between an upper electrode 312 and a lower electrode 314. In a case in which a driving voltage is applied between the upper electrode 312 and the lower electrode 314, flexural deformation occurs in the piezoelectric element 310, and the vibrating plate 308 is deformed.

In a case in which the volume of the pressure chamber 300 is reduced by deformation of the vibrating plate 308, liquid in an amount corresponding to the decrease in volume of the pressure chamber 300 is jetted out through the nozzle unit 18A. After the liquid inside the pressure chamber 300 is jetted out, liquid is supplied to the pressure chamber 300 from the common flow channel 306 through the supply port 304.

The liquid mentioned herein is PEG in the form of liquid, which forms the PEG liquid droplets 14 shown in FIG. 1A.

The present embodiment describes a piezoelectric type liquid jetting head as an example; however, a thermal type liquid jetting head that utilizes a film boiling phenomenon of the liquid in the pressure chamber may also be applied.

Figure 13:
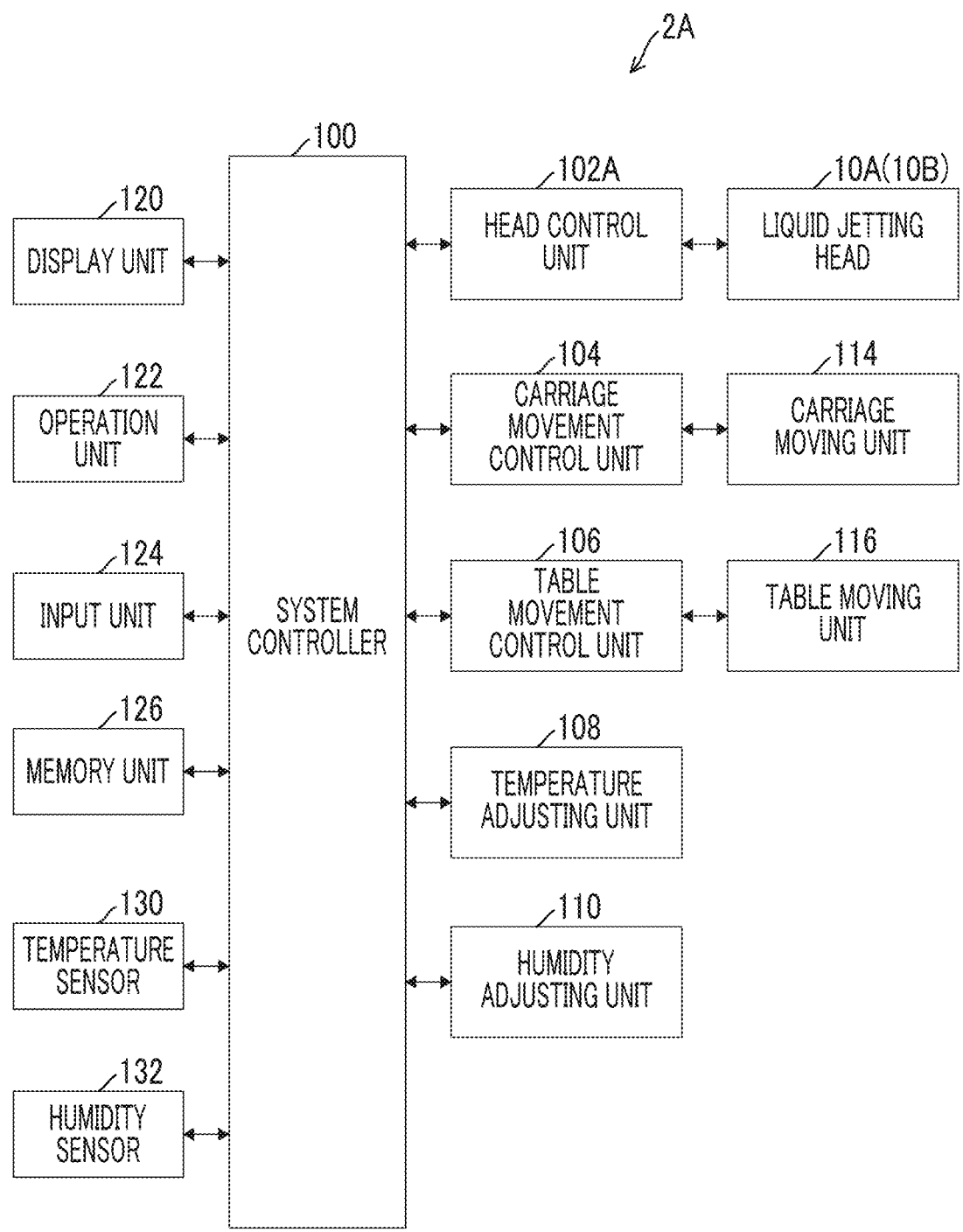
FIG. 13 is a block diagram of a control system in the polyethylene glycol structure forming unit illustrated in FIG. 10.

FIG. 13 is a block diagram of the control system in the polyethylene glycol structure forming unit illustrated in FIG. 10. The control system shown in FIG. 13 includes the control unit 80A shown in FIG. 10. The control system shown in FIG. 13 includes a head control unit 102A instead of the jetting control unit 102 of the control system of the PEG structure forming unit 2 shown in FIG. 6.

The head control unit 102A controls the jetting of the liquid jetting head 10A shown in FIG. 10, based on the control signals transmitted from the system controller 100. Other parts of the configuration of the control system shown in FIG. 13 are the same as the configuration of the control system shown in FIG. 6, and thus further explanation will not be given here.

[Explanation of Other Aspects of Method for Producing Gelatin Structure]

FIG. 14 is a flowchart showing the procedure of another aspect of the method for producing a gelatin structure. In FIG. 14, the same reference numerals will be assigned to the same processes as those shown in FIG. 3, and further explanation will not be repeated as appropriate. In the flowchart shown in FIG. 14, post-processing step S21 is added between the container removal step S20 and the freeze-drying step S22 shown in FIG. 3.

In the post-processing step S21 shown in FIG. 14, the solid gelatin 30A illustrated in FIG. 1H is processed into a predetermined shape. Subsequently, the solid gelatin 30A obtained after the post-processing is subjected to a freeze-drying treatment in the freeze-drying step S22.

An aspect of subjecting the gelatin structure 32 obtained after the freeze-drying treatment to post-processing can also be employed. The post-processing step S21 shown in FIG. 14 is a part of the constituent elements of the shaping step.

[Detailed Explanation of PEG Structure Formation]

Next, the formation of a PEG structure will be described in detail. Hereinafter, jettability of PEG at the time of forming a PEG structure, and laminating properties of PEG liquid droplets will be described in detail.

<Evaluation of Jettability>

Figure 15A:
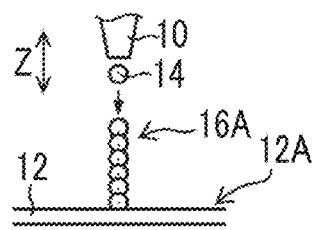
FIG. 15A is a schematic diagram illustrating the formation of a single polyethylene glycol pillar.

FIG. 15A to FIG. 15D are explanatory diagrams for an evaluation of the laminating properties of polyethylene glycol liquid droplets. FIG. 15A is a schematic diagram for the formation of a single polyethylene glycol pillar. In FIG. 15A, the formation of a single vertical PEG pillar 16A obtained by stacking PEG liquid droplets 14 is schematically illustrated.

As illustrated in FIG. 15A, first, one PEG liquid droplet 14 is jetted on a liquid landing surface 12A of a substrate 12, and the PEG droplet is hardened. A jet dispenser 10 is moved forward in the Z-direction, that is, in the direction of a line normal to the liquid landing surface 12A of the substrate 12, in which direction the jet dispenser 10 is separated away from the substrate 12, and while the distance between the PEG liquid droplet 14 and the jet dispenser 10 is maintained constant, jetting of PEG liquid droplets 14 is performed for a plurality of times. The direction of movement of the jet dispenser 10 is depicted using an arrow line in FIG. 15B.

In this way, a vertical PEG pillar 16A is formed along the direction of a line normal to the liquid landing surface 12A of the substrate 12.

Figure 15B:
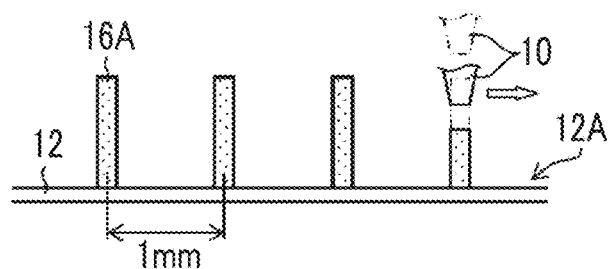
FIG. 15B is a schematic diagram illustrating the formation of a plurality of polyethylene glycol pillars.

FIG. 15B is a schematic diagram illustrating the formation of a plurality of polyethylene glycol pillars. A plurality of the vertical PEG pillars 16A shown in FIG. 15B were disposed at an equal interval by moving the jet dispenser 10 and the substrate 12 relative to each other along a direction parallel to the liquid landing surface 12A of the substrate 12. In the present embodiment, an example in which a plurality of vertical PEG pillars 16A are formed at an interval of 1 millimeters is disclosed.

The interval of disposition of a plurality of the vertical PEG pillars 16A can be set to any arbitrary value as long as it is a value larger than the diameter of adjacent vertical PEG pillars 16A.

The arrow line shown in FIG. 15B represents the direction of movement of the jet dispenser 10 in a plane parallel to the liquid landing surface 12A of the substrate 12. The direction of movement of the jet dispenser 10 may be the X-direction or the Y-direction as shown in FIG. 5. The direction of movement may also be an inclined direction that intersect the X-direction and the Y-direction.

In the present embodiment, the jetting speed for PEG in the jet dispenser 10 was set to 10 millimeters per second, the interval of jetting of PEG was set to 5 seconds, and thus 40 droplets of PEG liquid droplets 14 were jetted out at the position of formation of a single vertical PEG pillar 16A.

The results for the evaluation of jettability of PEG are presented in [Table 1].

TABLE 1

|  | 60° C. | 100° C. | 130° C. |
|---|---|---|---|
| PEG100000 alone | C | C | C |
| PEG40000 alone | C | B | B |
| 35000 < molecular weight < 55000 |  | (100000 or more) | (35000) |
| PEG20000 alone | C | B | B |
| 15000 < molecular weight < 25000 |  | (9800) | (5700) |
| PEG10000 alone | A | A | A |
| 8800 < molecular weight < 112000 | (5000) | (770) | (550) |
| PEG6000 alone | A | A | A |
| 5500 < molecular weight < 6500 | (5000) | (851) | (461) |
| PEG4000 alone | A | A | A |
| 2700 < molecular weight < 4300 | (2460) | (147) | (126) |

Grade A in [Table 1] represents that normal jetting is enabled in the temperature adjustable range of the jet dispenser 10. Normal jetting implies that PEG liquid droplets having a volume in a predetermined range have landed on the substrate according to the command for jetting.

Grade B represents the case in which normal jetting could not be achieved, and the case in which the PEG liquid droplets landed on the substrate; however, the volume of the PEG liquid droplets landed on the substrate was less than a predetermined volume, or the case in which the volume of the PEG liquid droplets landed on the substrate was larger than a value of less than the predetermined volume. Grade C represents the case in which any temperature higher than the melting point of the PEG is not included in the temperature adjustable range of the jet dispenser 10, and PEG does not melt.

In the evaluation of jettability disclosed in the present embodiment, a liquid jetting apparatus produced by mounting a jet dispenser 10 on a robot configured to be able to move the jet dispenser 10 and the substrate 12 shown in FIG. 15A in the X-direction, Y-direction, and Z-direction, was used.

Regarding the robot, a SHOT MINI200ΩX manufactured by Musashi Engineering, Inc. was used. Regarding the jet dispenser, an AEROJET MJET-A manufactured by Musashi Engineering, Inc. was used. Regarding the nozzle unit, a SNJ21-34G-SHN manufactured by Musashi Engineering, Inc. was used. The diameter of the nozzle unit is 0.07 millimeters. The term milli- is a prefixed unit representing $10^{-3}$.

Regarding the PEG used for the evaluation of jettability, polyethylene glycol 10000, polyethylene glycol 40000, polyethylene glycol 20000, polyethylene glycol 10000, polyethylene glycol 6000, and polyethylene glycol 4000, all manufactured by Wako Pure Chemical Industries, Ltd., were used. Hereinafter, polyethylene glycol will be described as PEG.

The average molecular weight distribution of PEG40000 is more than 35000 and less than 55000. The average molecular weight distribution of PEG20000 is more than 15000 and less than 25000.

The average molecular weight distribution of PEG10000 is more than 8800 and less than 11200. The average molecular weight distribution of PEG6000 is more than 5500 and less than 6500. The molecular weight distribution of PEG4000 is more than 2700 and less than 4300. The average molecular weight distribution corresponds to the molecular weight distribution.

Here, regarding the measurement of the average molecular weight distribution of each PEG, the hydroxyl group value is determined according to a neutralization titration method, and the average molecular weight distribution is calculated by the formula: $K=(56106/P) \times 2$, wherein K represents the average molecular weight, and P represents the hydroxyl group value. 56106 is a factor attributed to potassium hydroxide molecules. 2 is the number of hydroxyl groups.

Regarding the neutralization titration method, the neutralization titration method of section 7.1 in the testing method of JIS K 0070 is applicable. Meanwhile, JIS is an abbreviation for the Japanese Industrial Standards.

That is, the average molecular weight distribution of each PEG can be determined by GPC measurement or HPLC measurement, by which the molecular weight is calculated based on the hydroxyl group value. GPC is an abbreviation for Gel Permeation Chromatography. HPLC is an abbreviation for High Performance Liquid Chromatography.

The column for 60° C. in [Table 1] represents the evaluation of wettability in the case in which the temperature of each PEG was 60° C. The column for 100° C. in [Table 1] represents the evaluation of jettability in the case in which the temperature of each PEG was 100° C. The column for 130° C. in [Table 1] represents the evaluation of jettability in the case in which the temperature of each PEG was 130° C. The values given in the parentheses in the various columns represent viscosity. The unit for viscosity is milliPascal·second. The viscosity of PEG40000 at 100° C. was 100,000 milliPascal·second or more, which was the upper limit of the measurable range.

The viscosity of PEG according to the present embodiment is a measured value obtained using a viscometer. In the evaluation of jetting characteristics according to the present embodiment, and the evaluation of laminating properties that will be described below, an EMS viscometer EMS-1000 manufactured by Kyoto Electronics Manufacturing Co., Ltd. can be used as the viscometer. EMS is an abbreviation for Electro-Magnetically Spinning.

The method for measurement employed by the EMS viscometer EMS-1000 is an electron spinning method. For the adjustment of temperature of PEG, a temperature elevating apparatus capable of setting the temperature to the range of from 0° C. to 200° C. was used. The temperature of PEG is the set value of temperature of the temperature elevating apparatus.

As shown in [Table 1], in a case in which the temperature of PEG is from 60° C. to 130° C., normal jetting of PEG10000 alone, PEG6000 alone, and PEG4000 alone is enabled. The upper limit of the viscosity range of PEG in this case is 5,000 milliPascal·second, and the lower limit is 126 milliPascal·second. Here, the phrase "PEG alone" means that the PEG is a PEG having a predetermined average molecular weight range, while the PEG is not a mixture with a PEG having a different molecular weight range.

In regard to the lower limit of the viscosity range in which normal jetting is enabled, the lower limit of the jetting range in which normal jetting is enabled was set to 100 milliPascal·second, which was a number obtained by rounding down the last two figures of the measured value, 126 milliPascal·second, considering that jetting generally becomes easier as the viscosity value is smaller.

PEG10000, PEG6000, and PEG4000 are first polyethylene glycols having a molecular weight distribution that can be adjusted to a viscosity range in which jetting of the PEG alone is enabled, and these constitute an aspect of the first biocompatible material.

Meanwhile, PEG100000, PEG40000, and PEG20000 cannot be used alone to perform normal jetting in the temperature range of 60° C. or higher and lower than 130° C. This is speculated to be because the viscosity of the PEG exceeds the upper limit of viscosity at which normal jetting can be carried out.

PEG100000, PEG40000, and PEG20000 are second polyethylene glycols having a molecular weight distribution that cannot be adjusted to a viscosity range in which jetting of the PEG alone is enabled, and these constitute an aspect of the second biocompatible material.

In the evaluation of jettability according to the present embodiment, a PEG obtained by mixing PEG20000 and PEG4000 was used. As the PEG obtained by mixing PEG20000 and PEG4000, a PEG obtained by mixing 80 percent by mass of PEG20000 and 20 percent by mass of PEG4000; a PEG obtained by mixing 70 percent by mass of PEG20000 and 30 percent by mass of PEG4000; a PEG obtained by mixing 50 percent by mass of PEG20000 and 50 percent by mass of PEG4000; and a PEG obtained by mixing 30 percent by mass of PEG20000 and 70 percent by mass of PEG 4000 were used.

The results for the evaluation of jettability for the four kinds of PEG are presented in the following [Table 2].

TABLE 2

|  | 60° C. | 100° C. | 130° C. |
| --- | --- | --- | --- |
| PEG20000 and PEG4000 mixed Mixing ratio 80:20 | B (32100) | A (8920) | A (4310) |
| PEG20000 and PEG4000 mixed Mixing ratio 70:30 | B (25900) | A (7750) | A (3680) |
| PEG20000 and PEG4000 mixed Mixing ratio 50:50 | B (22030) | A (6750) | A (3630) |
| PEG20000 and PEG4000 mixed Mixing ratio 30:70 | B (13600) | A (4390) | A (2410) |

In a case in which the temperature of PEG is from 100° C. to 130° C., the PEG's obtained by mixing PEG20000 with PEG4000 are such that normal jetting is enabled in all of the four kinds described above. The upper limit of the viscosity range of the PEG in this case was 8920 milliPascal·second, and the lower limit is 2410 milliPascal·second.

By mixing PEG20000 that cannot be adjusted to a viscosity range in which normal jetting of the PEG alone is enabled under the temperature conditions of from 60° C. to 130° C., with PEG4000 that can be adjusted to a viscosity range in which normal jetting of the PEG alone is enabled under the temperature conditions of from 60° C. to 130° C., and adjusting the temperature of the PEG's thus mixed, normal jetting is made possible. In the present embodiment, it was confirmed that normal jetting is enabled with four kinds of PEG's having different mixing ratios as shown in [Table 2], the PEG's being mixtures of PEG20000 and PEG4000.

By mixing a PEG that cannot be adjusted to a viscosity range in which normal jetting of the PEG alone is enabled under the temperature conditions of from 60° C. to 130° C., at least one kind of PEG that can be adjusted to a viscosity range in which normal jetting of the PEG alone is enabled under the temperature conditions of from 60° C. to 130° C., with the above-mentioned PEG, and adjusting the temperature range of the PEG's thus mixed, a PEG enabling normal jetting is obtained.

As shown in [Table 2], in a case in which the temperature of PEG is from 100° C. to 130° C., normal jetting is enabled in a case in which PEG20000 with mixed with PEG4000. The upper limit of the viscosity range of the PEG in this case is 8920 milliPascal·second, and the lower limit is 2410 milliPascal·second.

For the upper limit of the viscosity range enabling normal jetting, a value that was almost a median value between the actual measured value, 8920 milliPascal·second, which was the viscosity upper limit enabling normal jetting, and the actual measured value, 13600 milliPascal·second, which was the viscosity lower limit that does not enable normal jetting, the value being obtained by rounding down the last four figures of the actual value, was employed in consideration of the reliability of temperature adjustment and the measurement error for viscosity, and the employed value was 10,000 milliPascal·second.

As the upper limit of the viscosity range enabling normal jetting, 9,000 milliPascal·second, which is a value obtained by rounding off the last three figures of the actual measured value, 8920 milliPascal·second, can be employed. Furthermore, 8,000 milliPascal·second, which is a value obtained by rounding down the last three figures of the actual measured value, 8920 milliPascal·second, can be employed.

In regard to the lower limit of the viscosity range enabling normal jetting, the lower limit of the jetting range enabling normal jetting was set to 100 milliPascal·second, which was obtained by rounding down the last two figures of the measured value described in [Table 1], 126 milliPascal·second, considering that jetting generally becomes easier as the viscosity value is smaller.

A PEG obtained by mixing 80 percent by mass of PEG20000 with 20 percent by mass of PEG4000; a PEG obtained by mixing 70 percent by mass of PEG20000 with 30 percent by mass of PEG4000; a PEG obtained by mixing 50 percent by mass of PEG20000 with 50 percent by mass of PEG4000; or a PEG obtained by mixing 30 percent by mass of PEG20000 with 70 percent by mass of PEG4000, are third polyethylene glycols obtained by mixing the first biocompatible material is incorporated at a proportion of from 20 percent by mass to 80 percent by mass into the second biocompatible material, the third polyethylene glycol being an aspect of the third biocompatible material.

In regard to the difference between the viscosity range enabling jetting of a PEG alone as shown in [Table 1] and the viscosity range enabling jetting of a mixed PEG as shown in [Table 2], it is speculated that the difference is a result of the effects of the difference between the hardening rates of a PEG alone and a mixed PEG, the difference in the temperature difference between the temperature at the time of jetting and the temperature at which hardening begins, and the like.

In the present embodiment, the temperature adjustment range of PEG was set to a range of from 60° C. to 130° C.; however, the temperature adjustment range of PEG is a temperature range including temperatures that are higher than the melting point of the PEG, and a temperature range in which the temperature of the jet dispenser is adjustable according to the temperature adjustment ability of the jet dispenser, can be adopted.

The temperature range in which the temperature of the jet dispenser is adjustable can be modified as appropriate, in consideration of the durability of members that are brought into contact with PEG or PEG liquid droplets, such as a nozzle unit and a substrate, or the ability to maintain the temperature at the nozzle unit constant.

The temperature range in which the temperature of the jet dispenser is adjustable corresponds to a range in which the temperature of the PEG jetted out through a nozzle unit is adjustable.

<Evaluation of Laminating Properties>

Next, an evaluation of the laminating properties of PEG liquid droplets will be explained. An evaluation of the laminating properties was performed in a case in which the results of the evaluation of jettability of PEG liquid droplets shown in [Table 1] and [Table 2] are A, that is, for PEG's that are capable of normal jetting.

Figure 15C:
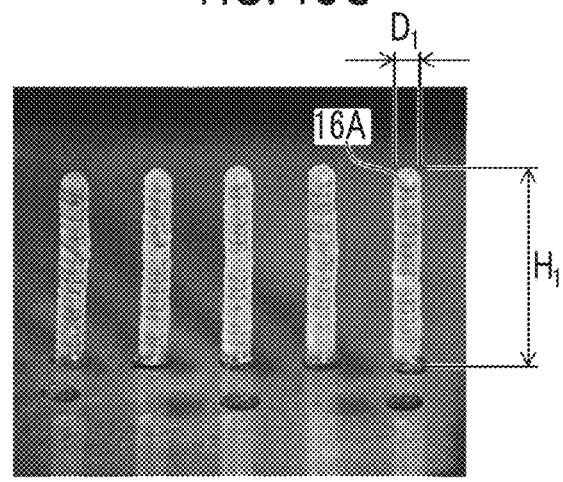
FIG. 15C is an electron microscopic photograph showing vertical polyethylene glycol pillars in a case in which a polyethylene glycol obtained by mixing PEG20000 and PEG4000 was used.

FIG. 15C is an electron microscopic photograph showing vertical PEG pillars in a case in which a PEG obtained by mixing PEG20000 with PEG4000 was used. The mixing ratio between PEG20000 and PEG4000 for the vertical PEG pillars 16A shown in FIG. 15C is 30 percent by mass of PEG20000 to 70 percent by mass of PEG4000.

The actual measured value of the width D1 of the vertical PEG pillars 16A shown in FIG. 15C is 0.21 millimeters, and the height is 1.33 millimeters. The vertical PEG pillars 16A shown in FIG. 15C are so stable that the vertical PEG pillars do not collapse and break in the middle even if pressed with a finger, and the contact portions between the vertical PEG pillars 16A and the substrate 12 are not detached from the substrate 12.

Figure 15D:
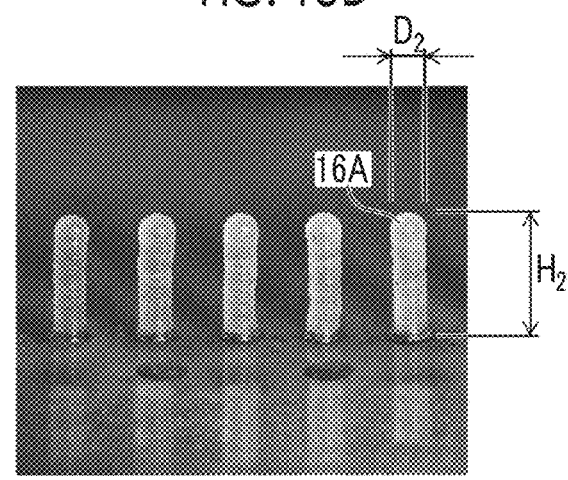
FIG. 15D is an electron microscopic photograph showing vertical polyethylene glycol pillars in a case in which PEG 4000 was used alone.

FIG. 15D is an electron microscopic photograph showing vertical PEG pillars in a case in which PEG4000 was used alone. The actual measured value of the width D2 of the vertical PEG pillars 16A shown in FIG. 15D is 0.26 millimeters, and the actual measured value of the height H2 is 0.86 millimeters.

The vertical PEG pillars 16A obtained in the case of using PEG4000 alone as shown in FIG. 15D have a large actual measured value of the width D2 and a small actual measured value of the height H2, compared to the vertical PEG pillars 16A obtained in the case of using a PEG obtained by mixing PEG20000 with PEG4000 as shown in FIG. 15C. That is, the vertical PEG pillars 16A exhibit the following relations: D1<D2 and H1>H2.

This is speculated to be because PEG4000 alone has low viscosity and superior wet-spreading properties on the liquid landing surface 12A of the substrate 12, compared to a PEG obtained by mixing PEG20000 alone with PEG4000 alone.

In the present embodiment, the results obtainable in a case in which the temperature of PEG is 100° C. Although not shown in the diagram, it was confirmed that even in a case in which the temperature of PEG was 130° C., results similar to those obtained in the case in which the temperature of PEG was 100° C. were obtained. Furthermore, it was confirmed that similar results were obtained with the four kinds of PEG's having different mixing ratios as indicated in [Table 2].

<Evaluation of Laminating Properties in Inclined Direction>

Figure 16A:
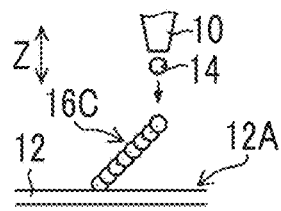
FIG. 16A is a schematic diagram illustrating the formation of a single inclined polyethylene glycol pillar.

FIG. 16A to FIG. 16D are explanatory diagrams for an evaluation of the laminating properties in an inclined direction of polyethylene glycol liquid droplets. FIG. 16A is a schematic diagram illustrating the formation of a single inclined polyethylene glycol pillar. In FIG. 16A, the formation of an inclined PEG pillar 16C by laminating PEG liquid droplets 14 in an inclined direction is schematically depicted. The inclined PEG pillar 16C corresponds to an inclined portion.

As shown in FIG. 16A, first, one droplet of PEG liquid droplet 14 is jetted out on a liquid landing surface 12A of a substrate 12, and the PEG droplet is hardened. A jet dispenser 10 is moved in an inclined direction having a forward component in the Z-direction and a component in a direction parallel to the liquid landing surface 12A of the substrate 12, the distance between the PEG liquid droplet 14 and the jet dispenser 10 is maintained constant, and while the jet dispenser 10 is shifted at a certain distance in a single direction parallel to the liquid landing surface 12A of the substrate 12, jetting of the PEG liquid droplets 14 is performed a plurality of times. The direction of movement of the jet dispenser 10 is depicted in FIG. 16B using an arrow line.

Then, there is formed an inclined PEG pillar 16C in which PEG liquid droplets 14 shown in FIG. 16A are laminated obliquely, the inclined PEG pillar 16C following a direction having a component in the direction of a line normal to the liquid landing surface 12A of the substrate 12 and a component in a direction parallel to the liquid landing surface 12A of the substrate 12.

Figure 16B:
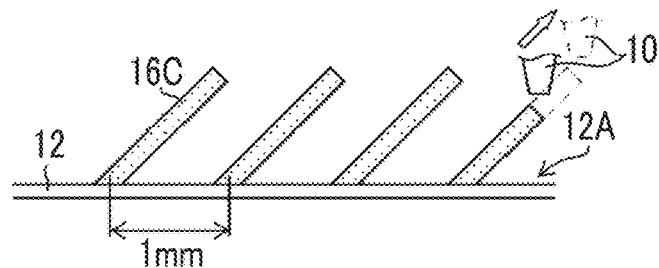
FIG. 16B is a schematic diagram illustrating the formation of a plurality of inclined polyethylene glycol pillars.

FIG. 16B is a schematic diagram illustrating the formation of a plurality of inclined polyethylene glycol pillars. In the formation of a plurality of the inclined PEG pillars 16C shown in FIG. 16B, a first droplet of the PEG liquid droplet 14 is landed at each of the positions of formation of a plurality of PEG pillars on the liquid landing surface 12A of the substrate 12, the first droplet of the PEG liquid droplet 14 is hardened, and a second PEG liquid droplet 14 is landed on the first PEG liquid droplet 14 at each of the positions of formation of the PEG pillars.

The second PEG liquid droplet 14 is such that the position of landing is shifted by 0.075 millimeters with respect to the first PEG liquid droplet 14 in a direction parallel to the liquid landing surface 12A of the substrate 12. The second PEG liquid droplet 14 is hardened, moving and jetting of the jet dispenser 10 are further repeated, and thereby a plurality of inclined PEG pillars 16C as shown in FIG. 16B are formed. The interval of disposition of a plurality of the inclined PEG pillars 16C is 1 millimeters.

Figure 16C:
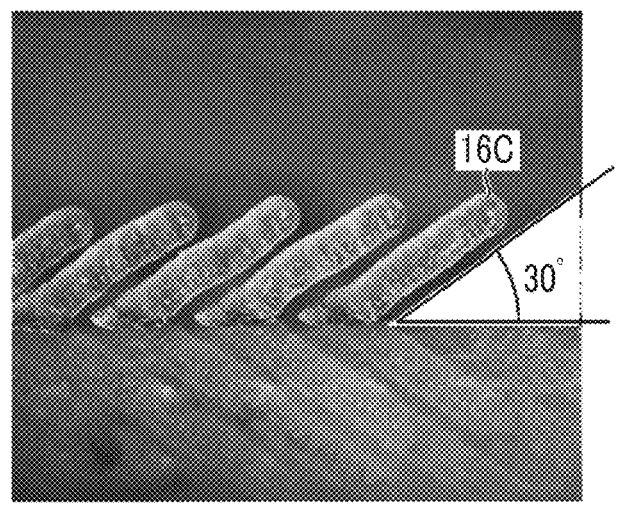
FIG. 16C is an electron microscopic photograph showing inclined polyethylene glycol pillars in a case in which a polyethylene glycol obtained by mixing PEG20000 and PEG4000 was used.

FIG. 16C is an electron microscopic photograph showing inclined polyethylene glycol pillars obtained in a case in which a polyethylene glycol obtained by mixing PEG20000 with PEG4000 was used. The mixing ratio between PEG20000 and PEG4000 in the inclined PEG pillars 16C shown in FIG. 16C is 30 percent by mass of PEG20000 to 70 percent by mass of PEG4000.

As shown in FIG. 16C, it was confirmed that inclined PEG pillars 16C having an angle of inclination of 30 degrees with respect to the liquid landing surface 12A of the substrate 12 can be formed using a PEG obtained by mixing PEG20000 with PEG4000.

FIG. 16C shows the case in which the temperature of PEG is 100° C.; however, it was confirmed that results similar to those obtained in the case in which the temperature of PEG was 130° C. were obtained. Furthermore, it was confirmed that similar results are obtained for the four kinds of PEG's shown in [Table 2].

Figure 16D:
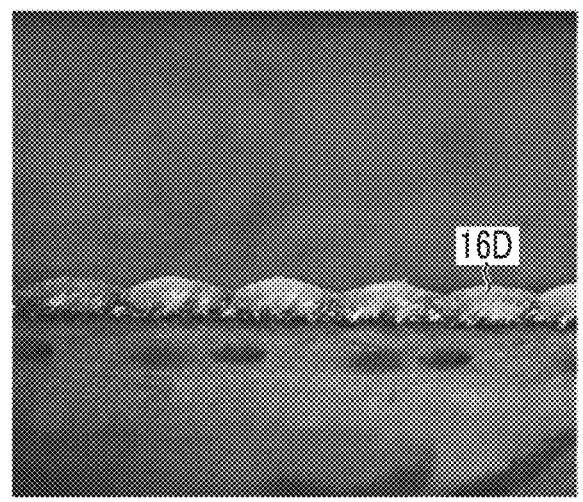
FIG. 16D is an electron microscopic photograph showing the results obtainable in the case of PEG4000 alone.

FIG. 16D is an electron microscopic photograph showing the results obtained in the case of PEG4000 alone. In the case of PEG4000 alone as shown in FIG. 16D, since the viscosity of PEG was low, and PEG was likely to hang down, the inclined PEG pillars 16C inclined in the direction of inclination shown in FIG. 16D could not be formed. The reference numeral 16D of FIG. 16D illustrates a plurality of PEG liquid droplets that have hung and coalesced on the liquid landing surface 12A of the substrate 12.

Although not shown in the diagram, an evaluation of whether the formation of inclined PEG pillars 16C having an angle of inclination of 30 degrees with respect to the liquid landing surface 12A of the substrate 12 is possible, was performed from a viewpoint similar to that of the formation of inclined PEG Pillars 16C having an angle of inclination of 60 degrees with respect to the liquid landing surface f the substrate.

The results for the evaluation of laminating properties are presented in the following [Table 3].

TABLE 3

| | Lamination in vertical direction | 60-degree inclined lamination | 30-degree inclined lamination |
| --- | --- | --- | --- |
| First PEG | 100 or more 5000 or less | 4000 or more 5000 or less | Not available |
| Third PEG | 100 or more 10000 or less | 500 or more 10000 or less | 2000 or more 10000 or less |

Here, the term first PEG used in [Table 3] represents the first polyethylene glycol. The first polyethylene glycol is a generic name for PEG10000 alone, PEG6000 alone, or PEG4000 alone.

The term third PEG used in [Table 3] represents the third polyethylene glycol. The value ranges shown in [Table 3] represent the viscosity of PEG. The unit is milliPascal·second.

The term lamination in vertical direction used in [Table 3] implies that vertical PEG pillars 16A can be formed along the direction of a line normal to the liquid landing surface 12A of the substrate 12.

The term 60-degree inclined lamination used in [Table 3] implies that inclined PEG pillars 16C can be formed along the direction of an angle of inclination of 60 degrees with respect to a direction parallel to the liquid landing surface 12A of the substrate 12.

The term 30-degree inclined lamination used in [Table 3] implies that inclined PEG pillars 16C can be formed along the direction of an angle of inclination of 30 degrees with respect to a direction parallel to the liquid landing surface 12A of the substrate 12.

In regard to the first PEG, in a case in which the viscosity range is from 100 milliPascal·second to 5,000 milliPascal·second, vertical PEG pillars 16A can be formed along the direction of a line normal to the liquid landing surface 12A of the substrate 12.

In regard to the first PEG, in a case in which the viscosity range is from 4000 milliPascal·second to 5,000 milliPascal·second, inclined PEG pillars 16C can be formed along the direction of an angle of inclination of 60 degrees with respect to a direction parallel to the liquid landing surface 12A of the substrate 12.

Meanwhile, in regard to the first PEG, there is no viscosity range in which the formation of inclined PEG pillars 16C along the direction of an angle of inclination of 30 degrees with respect to a direction parallel to the liquid landing surface 12A of the substrate 12.

In regard to the third PEG, in a case in which the viscosity range is from 100 milliPascal·second to 10,000 milliPascal·second, vertical PEG pillars 16A can be formed along the direction of a line normal to the liquid landing surface 12A of the substrate 12.

In regard to the third PEG, in a case in which the viscosity range is from 500 milliPascal·second to 10,000 milliPascal·second, inclined PEG pillars 16C can be formed along the direction of an angle of inclination of 60 degrees with respect to a direction parallel to the liquid landing surface 12A of the substrate 12.

In regard to the third PEG, in a case in which the viscosity range is from 2,000 milliPascal·second to 10,000 milliPascal·second, inclined PEG pillars 16C can be formed along the direction of an angle of inclination of 30 degrees with respect to a direction parallel to the liquid landing surface 12A of the substrate 12.

That is, in regard to the third PEG, in a case in which the viscosity range is from 2,000 milliPascal·second to 10,000 milliPascal·second, inclined PEG pillars 16C can be formed along the direction of an angle of inclination of 30 degrees or more and less than 60 degrees with respect to a direction parallel to the liquid landing surface 12A of the substrate 12.

In the present embodiment, viscosity range conditions of laminatable PEG were induced for discrete molecular weights and discrete temperatures; however, when it is considered that the viscosity of PEG undergoes a simple increase or a simple decrease with respect to the increase or decrease of the molecular weight, and the viscosity of PEG undergoes a simple decrease or a simple increase with respect to the increase or decrease of temperature, it can be predicted that results similar to discrete values are obtained also for the molecular weight and temperature between discrete values.

The viscosity range shown in [Table 3] is induced by appropriately rounding down or rounding off the measured values, in consideration of the measurement error, the interval of discrete values used for the measurement, and the like.

In connection with [Table 3], it is considered that the difference between the viscosity range capable of forming a laminate of the first PEG and the viscosity range capable of forming a laminate of the first PEG is attributed to the difference between the hardening rate of the first PEG and the hardening rate of the third PEG. The hardening rate of PEG after landing on the substrate tends to become higher as the molecular weight is larger.

However, it is contemplated that the third PEG has a high hardening rate after landing on the substrate compared to the first PEG, and a satisfactory laminate has been formed.

In the present embodiment, a mixed PEG of PEG20000 and PEG4000 has been mentioned as an example of the third PEG; however, it is also possible to use a mixed PEG of PEG20000 and PEG6000, a mixed PEG of PEG20000 and PEG10000, or the like as the third PEG.

That is, the temperature range capable of adjusting temperature for the jet dispenser is a temperature range including temperatures that are higher than the melting point of the PEG, and as long as the viscosity can be adjusted to the viscosity range shown in [Table 3], the type of the first PEG that constitutes the third PEG, and the type of the second PEG are not limited to the PEG mentioned in the present embodiment as an example.

[As to Substrate]

In the evaluation of the laminating properties of the PEG liquid droplets 14 disclosed in the present embodiment, a glass substrate was used as the substrate 12. In a case in which a material having water repellency with respect to PEG, such as an acrylic plate, is applied to the substrate 12, the adhesiveness of PEG to the substrate 12 is low, and at the contact surface between PEG and the substrate 12, collapse or breakage of PEG occurs. Therefore, a material having hydrophilicity with respect to PEG, such as glass, is applied to the substrate 12.

The hydrophilicity with respect to PEG according to the present embodiment implies a case in which the contact angle is more than 90 degrees, and the hydrophobicity with respect to PEG implies a case in which the contact angle is 90 degrees or less. In a case in which a material having water repellency with respect to PEG is applied to the substrate 12, a film of the material having hydrophobicity with respect to PEG is formed on the liquid landing surface 12A of the substrate 12.

In a case in which a material having hydrophobicity with respect to PEG is applied to the substrate 12, it is necessary to prevent the occurrence of collapse or breakage of PEG. Meanwhile, detachment between the substrate 12 and the PEG structure 20 is made easier.

[Operating Effect of Method for Producing Gelatin Structure According to Present Embodiment]

According to the method for producing a gelatin structure configured as described above, production of a PEG structure, which is a three-dimensional structure based on PEG that has high usage performance in the medical field is enabled by a droplet jetting type dispenser, or an inkjet head type liquid jetting head. By using this as a template, the formation of an inverted structure of gelatin is made possible.

that is, a PEG structure formed from PEG and having a three-dimensional structure is formed by adjusting the molecular weight distribution of PEG and the temperature range, and using a PEG having a viscosity that has been adjusted to a viscosity that enables jetting through a nozzle unit and enables lamination.

A gelatin structure having a three-dimensional shape of the PEG structure transferred to the interior of gelatin can be formed by attaching gelatin to the periphery of the PEG structure, subjecting the PEG structure to the action of the water of gelatin, and dissolving the PEG structure.

Regarding the PEG structure, a PEG structure following an inclined direction with respect to the liquid landing surface 12A of the substrate 12 can be formed by mixing a PEG having a molecular weight distribution that cannot be jetted out alone through a nozzle unit, with a PEG having a molecular weight distribution that can be jetted out alone through a nozzle unit, and adjusting the viscosity of the PEG.

[Explanation of Other Embodiments of Formation of PEG Structure]

Figure 17:
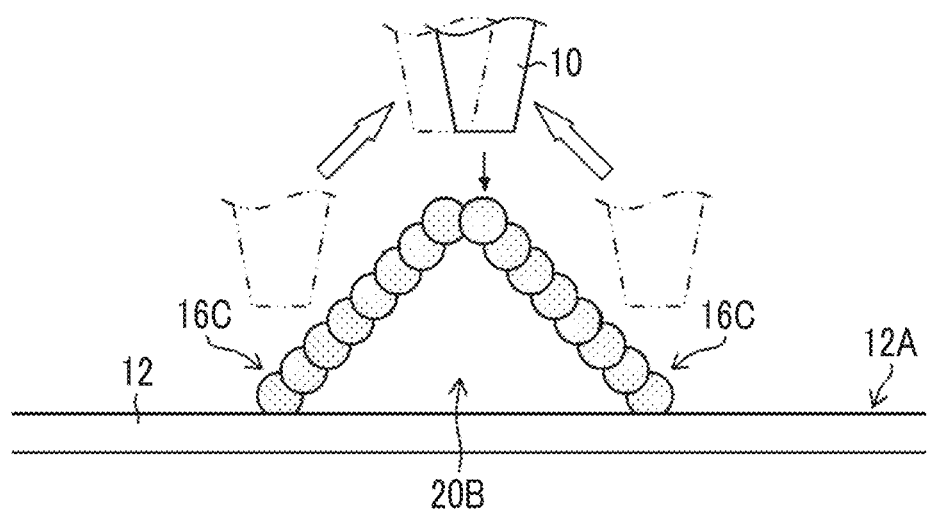
FIG. 17 is an explanatory diagram illustrating another embodiment of the formation of a polyethylene glycol structure.

FIG. 17 is an explanatory diagram illustrating another embodiment of the formation of a polyethylene glycol structure. FIG. 17 illustrates a PEG structure 20B having a structure in which two inclined PEG pillars 16C are joined at a position at which the distance from the substrate 12 becomes the maximum.

In FIG. 17, the procedure for forming the PEG structure 20B is schematically illustrated using a jet dispenser 10 illustrated using a two-dot broken line and arrow lines. In a case in which a liquid jetting head 10A including a plurality of nozzles as shown in FIG. 10 is applied to the formation of the PEG structure 20B shown in FIG. 17, the PEG structure 20B shown in FIG. 17 can be formed by changing the nozzle unit corresponding to the position of landing PEG, with a nozzle unit that is used for jetting, without changing the relative positions of the substrate 12 and the liquid jetting head 10A.

In the formation of the PEG structure 20B shown in FIG. 17, the diameter of the PEG liquid droplet 14 was set to a value of from 200 micrometers to 250 micrometers. The diameter of the PEG liquid droplet 14 is the diameter of a sphere induced by regarding a PEG liquid droplet 14 as a sphere, and determining the volume of the PEG liquid droplet 14 as the volume of a sphere.

The volume of the PEG liquid droplet 14 is from 100 picoliters to 10 nanoliters. Here, the term pico is a prefixed unit representing $10^{-12}$. The term nano is a prefixed unit representing $10^{-9}$.

Figure 18:
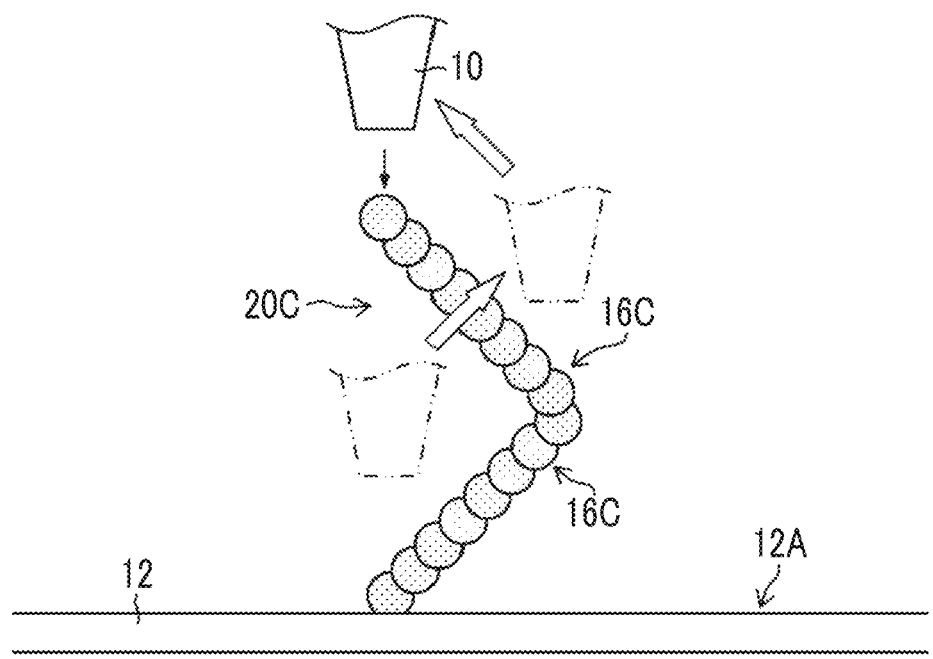
FIG. 18 is an explanatory diagram illustrating another embodiment of the formation of a polyethylene glycol structure.

FIG. 18 is an explanatory diagram of another embodiment of the formation of a polyethylene glycol structure. FIG. 18 illustrates a PEG structure 20C having a structure in which the direction of inclination has been changed at an intermediate position. In other words, the PEG structure 20C shown in FIG. 18 has a structure in which inclined PEG pillars 16C having different directions of inclination are joined in the direction of a line normal to the liquid landing surface 12A of the substrate 12.

Figure 19:
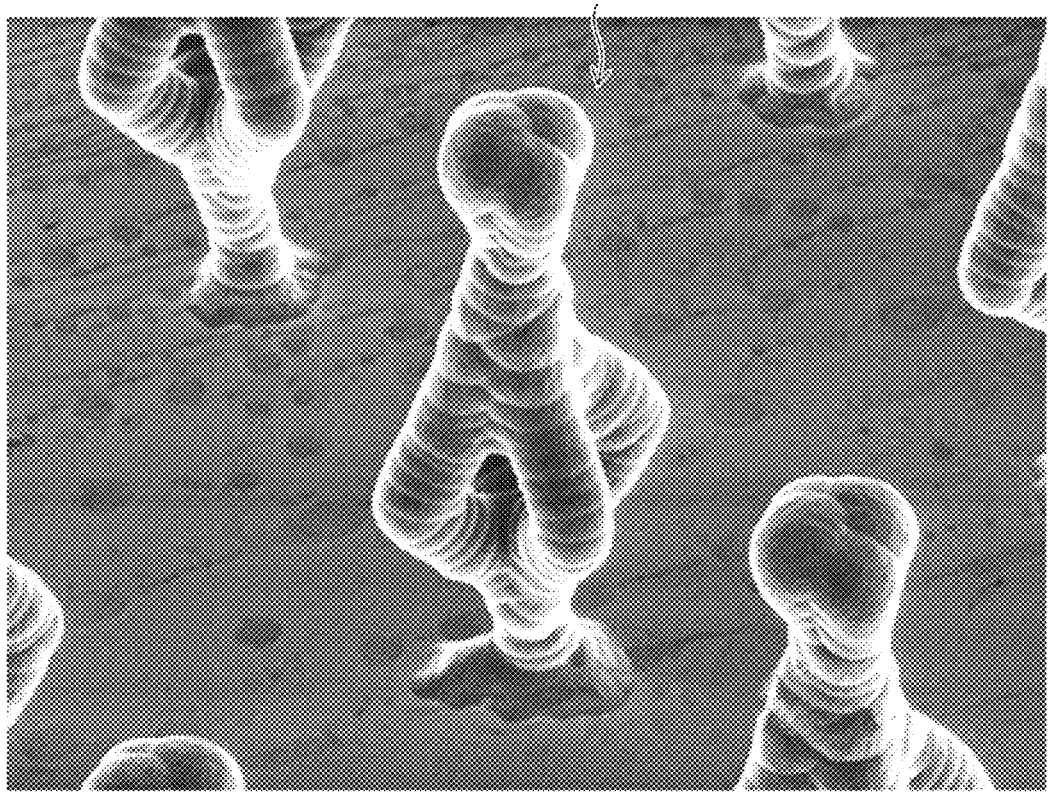
FIG. 19 is an explanatory diagram illustrating the formation of a polyethylene glycol structure having a quasi-octahedral structure.

FIG. 19 is an explanatory diagram showing the formation of a polyethylene glycol structure having a quasi-octahedral structure, and is an electron microscopic photograph of the PEG structure. The PEG structure 20D shown in FIG. 19 has a structure combining a plurality of the PEG structures 20B shown in FIG. 17, or a structure combining a plurality of the PEG structures 20C shown in FIG. 18.

The PEG structure 20D shown in FIG. 19 may be regarded as a quasi-octahedron, based on the eight faces that constitute the outer periphery of the PEG structure 20D.

Figure 20:
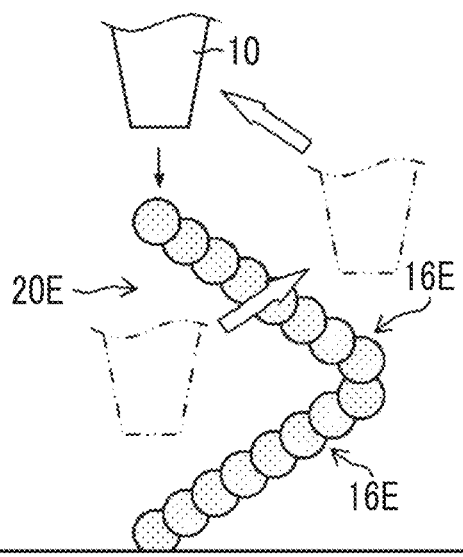
FIG. 20 is an explanatory diagram illustrating another embodiment of the formation of a polyethylene glycol structure.

FIG. 20 is an explanatory diagram of another embodiment for the formation of a polyethylene glycol structure. The PEG structure 20E shown in FIG. 20 uses inclined PEG pillars 16E having an angle of inclination that is less than the angle of inclination of the inclined PEG pillars 16C shown in FIG. 18 with respect to the liquid landing surface 12A of the substrate 12.

In the PEG structure 20E shown in FIG. 20, the angle formed by two inclined PEG pillars 16E is 90 degrees. 90 degrees as used herein includes substantial 90 degrees, with which an operating effect similar to that of 90 degrees is obtained, among angles less than 90 degrees and angles more than 90 degrees.

Furthermore, the PEG structure 20E illustrated in FIG. 20 is a PEG structure having a structure in which the angle of inclination is changed at an intermediate position, similarly to the PEG structure 20C illustrated in FIG. 18, and is a PEG structure having a structure in which inclined PEG pillars 16C having different directions of inclination are joined in the direction of a line normal to the liquid landing surface 12A of the substrate 12.

Figure 21:
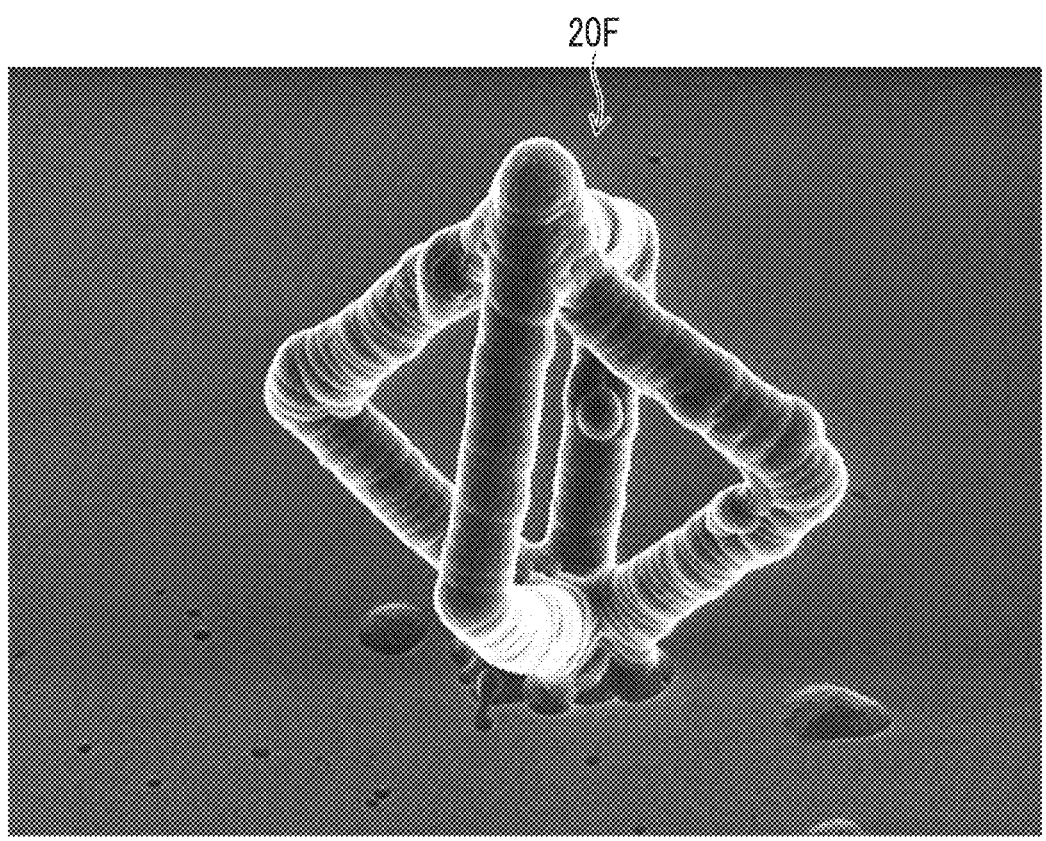
FIG. 21 is an explanatory diagram illustrating the formation of a polyethylene glycol structure having a quasi-regular octahedral structure.

FIG. 21 is an explanatory diagram for the formation of a polyethylene glycol structure having a quasi-regular octahedral structure, and is an electron microscopic photograph of a PEG structure. The PEG structure 20F shown in FIG. 21 has a structure combining a plurality of PEG structures 20E shown in FIG. 20.

The PEG structure 20F shown in FIG. 21 may be regarded as a quasi-regular octahedron, based on the eight faces that constitute the outer periphery of the PEG structure 20F.

Figure 22A:
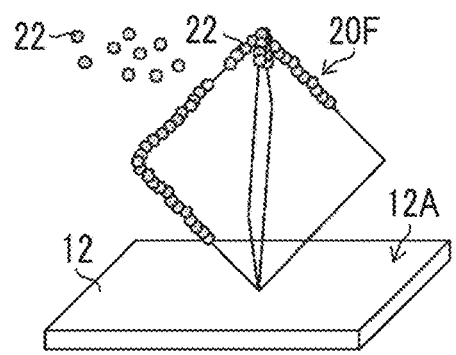
FIG. 22A is a schematic diagram illustrating a microparticulate gelatin attaching step.

FIG. 22A to FIG. 22D are schematic diagrams illustrating the procedure of the production of a gelatin structure using a polyethylene glycol structure having a quasi-regular octahedral structure. FIG. 22A is a schematic diagram illustrating a microparticulate gelatin attaching step. FIG. 22A illustrates a microparticulate gelatin attaching step of forming the PEG structure 20F shown in FIG. 21, which has a quasi-regular octahedral structure, on a liquid landing surface 12A of a substrate 12, and attaching microparticulate gelatin 22 thereto.

Figure 22B:
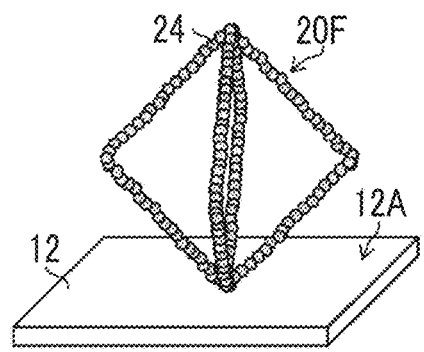
FIG. 22B is a schematic diagram illustrating a polyethylene glycol structure having a quasi-regular octahedral structure having a coating film formed thereon.

FIG. 22B is a schematic diagram illustrating a polyethylene glycol structure having a quasi-regular octahedral structure having a coating film formed thereon. FIG. 22B illustrates a state in which a coating film 24 has been formed by attaching microparticulate gelatin 22 to the entire periphery of the PEG structure 20F having a quasi-regular octahedral structure.

Figure 22C:
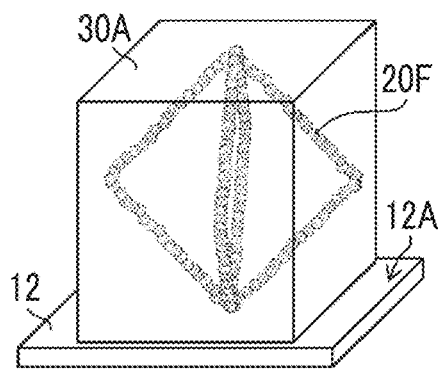
FIG. 22C is a schematic diagram illustrating solid gelatin.

FIG. 22C is a schematic diagram illustrating solid gelatin. FIG. 22C illustrates a state in which solid gelatin 30A has been formed by attaching a gelatin solution 30 to the PEG structure 20F shown in FIG. 22B, the PEG structure 20F having a coating film 24 formed over the entire periphery, and solidifying the gelatin solution 30.

Figure 22D:
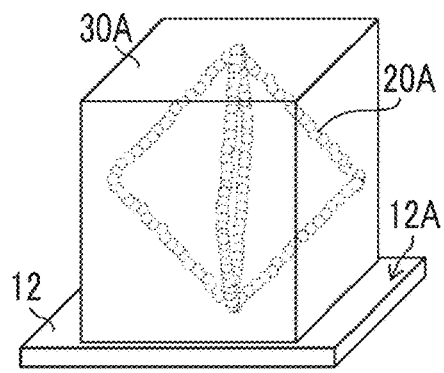
FIG. 22D is a schematic diagram illustrating solid gelatin in which the three-dimensional shape of a polyethylene glycol structure transferred to the interior.

FIG. 22D is a schematic diagram illustrating a solid gelatin having a three-dimensional shape of a polyethylene glycol structure transferred to the interior. FIG. 22D illustrates the solid gelatin 30A in which the PEG structure 20F shown in FIG. 22C has been dissolved, and thereby the three-dimensional shape of the PEG structure 20F has been transferred to the interior.

In this manner, a PEG structure having an arbitrary three-dimensional structure is used as a template, and a solid gelatin 30A having a hollow shape corresponding to the three-dimensional shape of a PEG structure is formed.

Figure 23A:
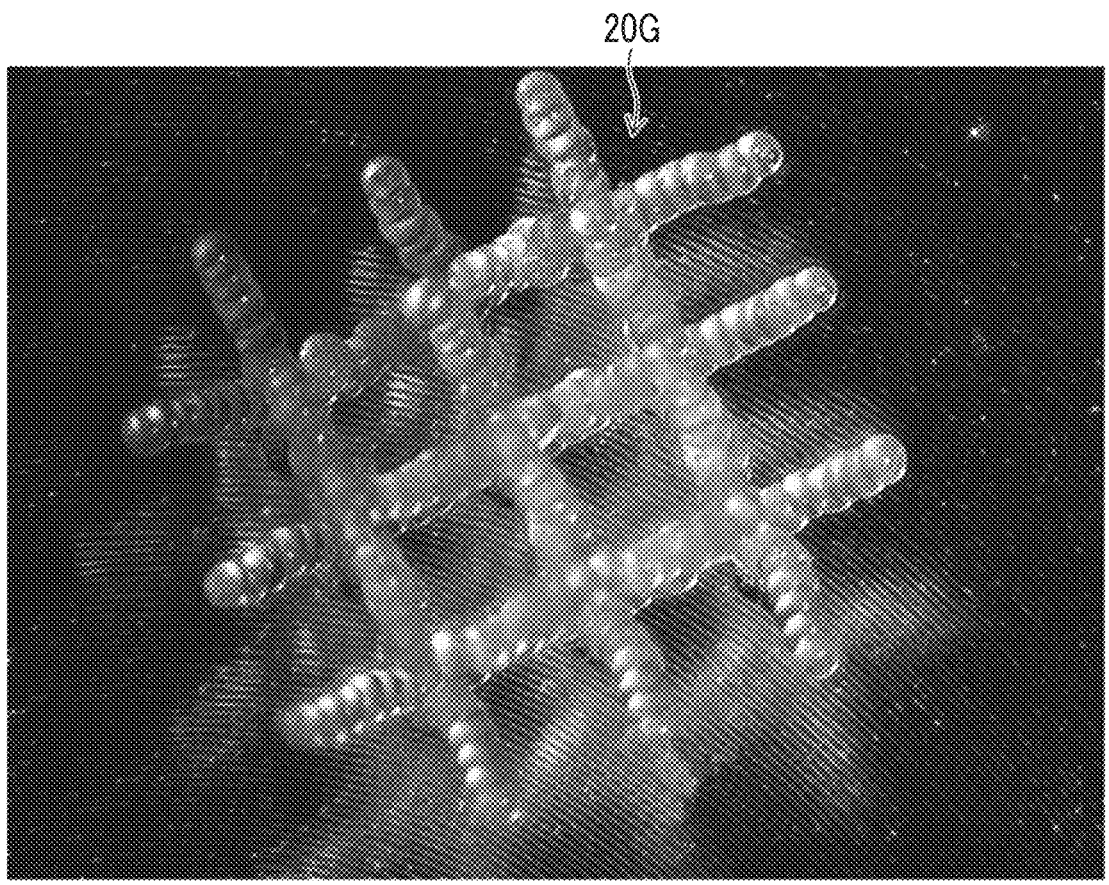
FIG. 23A is an electron microscopic photograph of a polyethylene glycol structure.

FIG. 23A to FIG. 25D are explanatory diagrams illustrating other embodiments of the formation of a PEG structure. FIG. 23A is an electron microscopic photograph of a PEG structure, and FIG. 23B is a schematic diagram illustrating a polyethylene glycol structure.

Figure 23B:
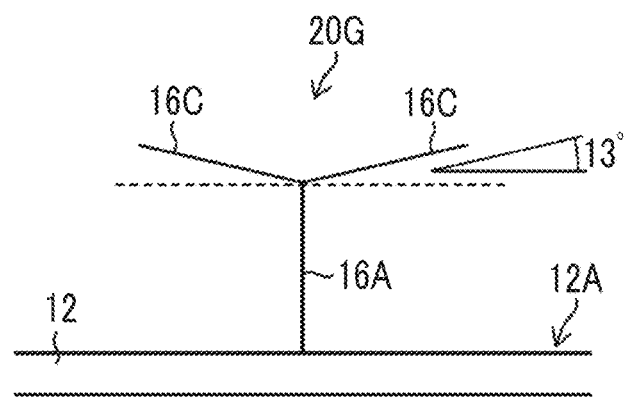
FIG. 23B is a schematic diagram illustrating a polyethylene glycol structure.

The PEG structure 20G shown in FIG. 23A and FIG. 23B has a shape in which the vertical PEG pillars 16A shown in FIG. 1A to FIG. 1I and two inclined PEG pillars 16C shown in FIG. 17 are combined.

Regarding the inclined PEG pillars 16C that constitute the PEG structure 20G shown in FIG. 23A and FIG. 23B, it is considered that the angle of inclination with respect to the liquid landing surface 12A of the substrate 12 is 13 degrees. The broken line shown in FIG. 23B represents a plane parallel to the liquid landing surface 12A of the substrate 12. That is, since formation of inclined PEG pillars 16C is made possible even in a case in which the angle of inclination with respect to the liquid landing surface 12A of the substrate 12 is less than 30 degrees, inclined PEG pillars 16C having an angle of inclination of 30 degrees or more with respect to the liquid landing surface 12A of the substrate 12 can be formed even in a case in which there are variations in the PEG.

The width of the vertical PEG pillars 16A that constitute the PEG structure 20G shown in FIG. 23A and FIG. 23B can be adjusted to be from 250 micrometers to 300 micrometers.

Figure 24A:
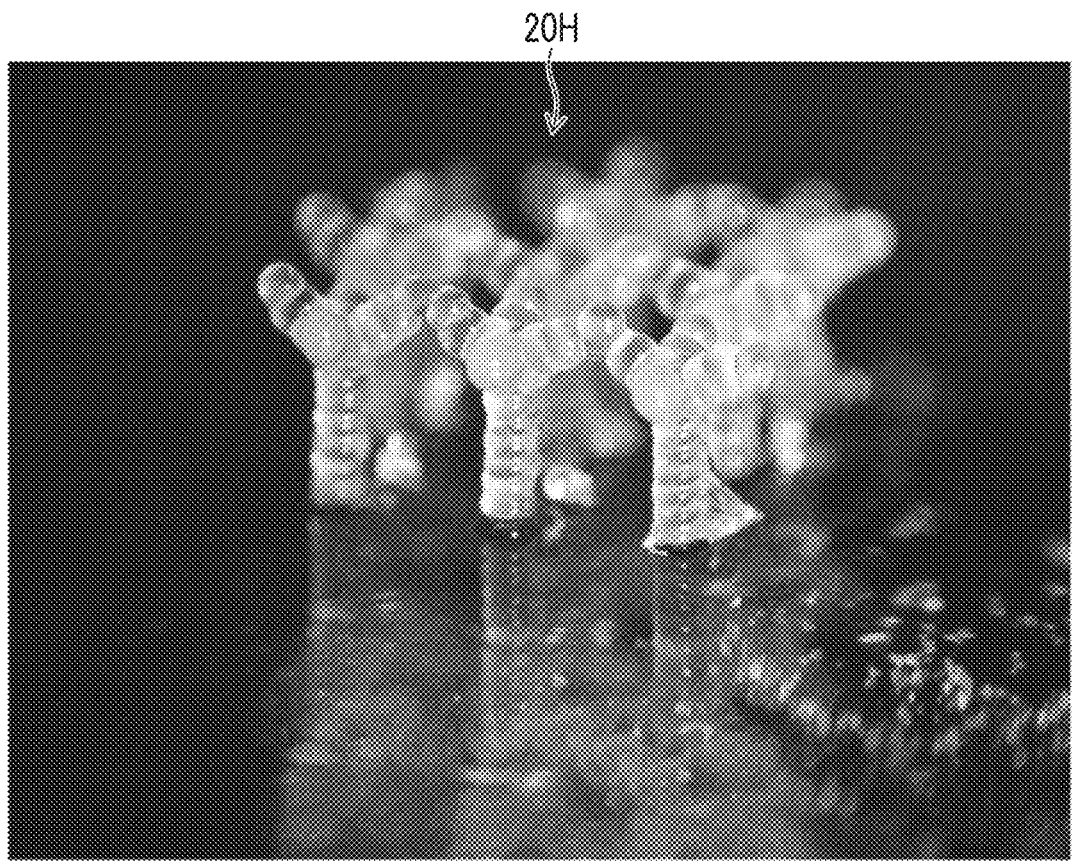
FIG. 24A is an electron microscopic photograph of a polyethylene glycol structure.
Figure 24B:
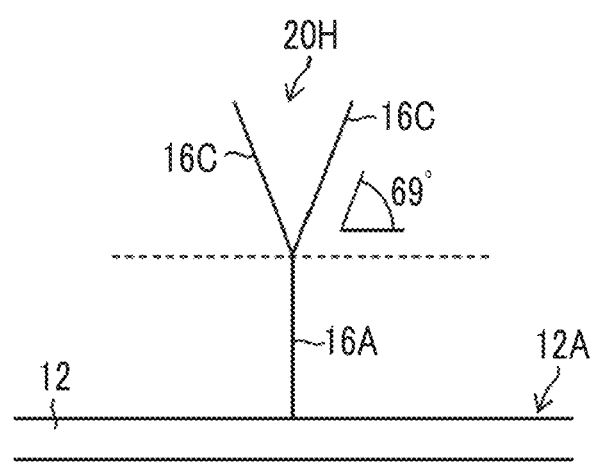
FIG. 24B is a schematic diagram illustrating a polyethylene glycol structure.

FIG. 24A and FIG. 24B are explanatory diagrams illustrating another embodiment of the formation of a polyethylene glycol structure. FIG. 24A is an electron microscopic photograph of a polyethylene glycol structure, and FIG. 24B is a schematic diagram of a polyethylene glycol structure.

Regarding the inclined PEG pillars 16C that constitute the PEG structure 20H shown in FIG. 24A and FIG. 24B, it is considered that the angle of inclination with respect to the liquid landing surface 12A of the substrate 12 is 69 degrees. The broken line depicted in FIG. 24B represents a plane parallel to the liquid landing surface 12A of the substrate 12.

The width of the vertical PEG pillars 16A that constitute the PEG structure 20H shown in FIG. 24A and FIG. 24B can be adjusted to be from 250 micrometers to 300 micrometers.

Figure 25A:
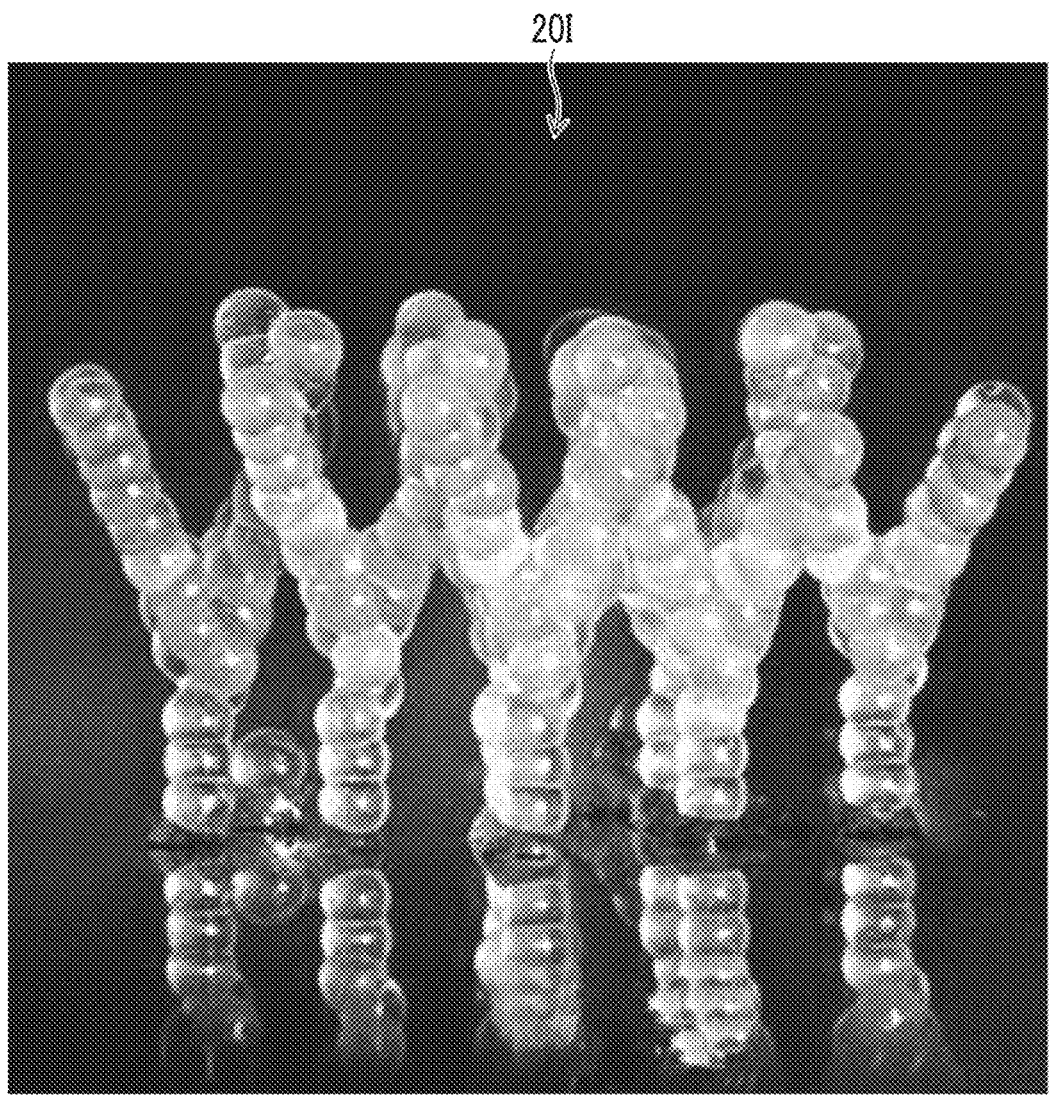
FIG. 25A is an electron microscopic photograph of a polyethylene glycol structure.
Figure 25B:
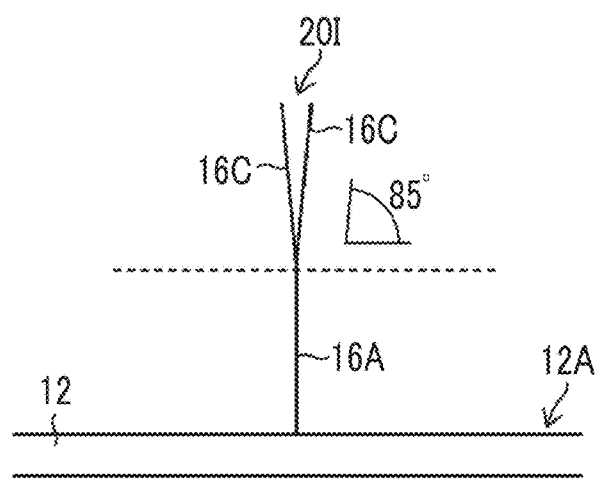
FIG. 25B is a schematic diagram illustrating a polyethylene glycol structure.

FIG. 25A and FIG. 25B are explanatory diagrams illustrating another embodiment of the formation of a polyethylene glycol structure. FIG. 25A is an electron microscopic photograph of a polyethylene glycol structure, and FIG. 25B is a schematic diagram of a polyethylene glycol structure.

Regarding the inclined PEG pillars 16C that constitute the PEG structure 20I shown in FIG. 25A and FIG. 25B, it is considered that the angle of inclination with respect to the liquid landing surface 12A of the substrate 12 is 85 degrees. The broken line depicted in FIG. 25B represents a plane parallel to the liquid landing surface 12A of the substrate 12.

The width of the vertical PEG pillars 16A that constitute the PEG structure 20I shown in FIG. 25A and FIG. 25B can be adjusted to be from 250 micrometers to 300 micrometers.

As shown in FIG. 17 to FIG. 21, a PEG structure 20 having an arbitrary three-dimensional shape can be formed by combining a plurality of inclined PEG pillars. Furthermore, as shown in FIG. 23A to FIG. 25B, a PEG structure 20 having an arbitrary three-dimensional shape can be formed by combining a vertical PEG pillar 16A and a plurality of inclined PEG pillars 16C. Although not shown in the diagrams, a PEG structure 20 having an arbitrary three-dimensional shape including the horizontal PEG pillars 16B shown in FIG. 1A to FIG. 1I can also be formed.

[Explanation of Gelatin]

Regarding the gelatin that can be applied to the method for producing a gelatin structure according to the present embodiment, natural gelatin can be applied. A variant having a difference of at least one amino acid residue from natural gelatin may also be used. Furthermore, it is preferable that the gelatin applicable to the method for producing a gelatin structure according to the present embodiment is a recombinant gelatin obtained by preparing a base sequence or an amino acid sequence in which modification of one or more base or one or more amino acid residue has been applied to the base sequence of the gene encoding collagen, or an amino acid sequence, the sequences having a sequence represented by Gly-X-Y six or more consecutive times; introducing the base sequence or amino acid sequence into an appropriate host by a conventional method; and expressing the base sequence or amino acid sequence. By using such a recombinant gelatin, a tissue repair ability can be enhanced, and also, various characteristics can be manifested compared to the case of using natural gelatin. For example, there is an advantage that inappropriate influence such as a rejection reaction by a living body can be avoided.

Examples of the recombinant gelatin that can be particularly preferably used include those disclosed in EP1014176A2, U.S. Pat. No. 6,992,172B, WO2004/85473A, WO2008/103041A, JP2010-519293A, JP2010-519252A, JP2010-518833A, JP2010-519251A, WO2010/128672A, WO2010/147109A, and JP2014-12114A.

As the recombinant gelatin, a recombinant peptide can be applied. A recombinant peptide means a polypeptide or a protein-like substance, which has an amino acid sequence similar to gelatin produced by a gene recombination technology.

A preferred example of the recombinant peptide that is applicable to the method for producing a gelatin structure according to the present embodiment is a recombinant peptide of the following aspect.

The recombinant peptide that is applicable to the method for producing a gelatin structure according to the present embodiment has excellent biocompatibility due to the performance intrinsic to natural gelatin, and has no risk of BSE or the like while having excellent non-infectiousness because the recombinant peptide is not derived from a natural material.

BSE is an abbreviation for Bovine Spongiform Encephalopathy and represents the mad cow disease.

Furthermore, since the recombinant peptide used in the present invention is uniform compared to natural materials and has a determined sequence, in view of strength, decomposability, and the like, it is possible to design the recombinant peptide precisely with less fluctuation by crosslinking or the like as will be described below.

The molecular weight of the recombinant peptide is preferably from 2,000 to 100,000. The molecular weight is more preferably from 2,500 to 95,000, even more preferably from 5,000 to 90,000, and most preferably from 10,000 to 90,000.

In the embodiments described in the present specification, polyethylene glycol has been taken as an example of the biocompatible material; however, any material for which the temperature in a jet dispenser or a liquid jetting head can be adjusted and normal jetting is enabled at an adjusted temperature, and a material that is thermoplastic and water-soluble can be applied as the biocompatible material.

In regard to the embodiments of the present invention described above, the constituent elements can be modified, added, or deleted as appropriate to the extent that the gist of the invention is maintained. The present invention is not intended to be limited to the embodiments described above, and many modifications can be made by those having ordinary skill in the pertinent art, within the scope of the technical idea of the invention.

EXPLANATION OF REFERENCES

1: gelatin structure production system
2: PEG structure forming unit
3: coating film forming unit
4: gelatin structure forming unit
5: gelatin attaching unit
6: hardening and dissolving unit
7: freeze-drying treatment unit
8: shaping unit
12: substrate
12A: liquid landing surface
14: PEG liquid droplet
16A: vertical PEG pillar
16B: horizontal PEG pillar
16C, 16E: inclined PEG pillar
18: nozzle unit
20: PEG structure
20A: hollow part
22: microparticulate gelatin
24: coating film
30: gelatin solution
30A: solid gelatin
32: gelatin structure
36: container
80, 80A: control unit

What is claimed is:

1. A method for producing a gelatin structure, the method comprising:
a biocompatible material structure forming step of jetting a liquid obtained by melting a biocompatible material that is solid in a temperature range of from 5° C. to 35° C. and is water-soluble and thermoplastic, in a droplet state through a nozzle unit, stacking the biocompatible material on a liquid landing surface, which is a surface of a substrate where liquid droplets land, and forming a biocompatible material structure having a three-dimensional structure formed from the biocompatible material;
a coating film forming step of forming a coating film containing gelatin, which coats the surface of the biocompatible material structure formed by the biocompatible material structure forming step;
a gelatin structure forming step of attaching gelatin on the periphery of the biocompatible material structure having the surface coated with the coating film formed by the coating film forming step, and forming a gelatin structure;
a shaping step of shaping the gelatin structure formed by the gelatin structure forming step into a predetermined shape; and
a dissolving step of subjecting the biocompatible material structure to the action of water to dissolve at least a portion of the biocompatible material structure, and thereby transferring a shape of the biocompatible material structure to an interior of the gelatin structure, wherein in the biocompatible material structure forming step, the biocompatible material structure is formed using a first biocompatible material having a molecular weight distribution that can be adjusted to a viscosity range enabling jetting of the biocompatible material alone in a temperature range in which the temperature of the biocompatible material jetted out through the nozzle unit can be adjusted, the first biocompatible material having a viscosity of from 100 milliPascal·second to 5,000 milliPascal·second, or a third biocompatible material obtained by mixing the first biocompatible material with a second biocompatible material having a molecular weight distribution that cannot be adjusted to a viscosity range enabling jetting of the biocompatible material alone in a temperature range in which the temperature of the biocompatible material jetted out through the nozzle unit can be adjusted, the third biocompatible material having a viscosity of from 100 milliPascal·second to 10,000 milliPascal·second.

2. The method for producing a gelatin structure according to claim 1, wherein in the biocompatible material structure forming step, the biocompatible material structure is formed using the first biocompatible material including polyethylene glycol, or the second biocompatible material including polyethylene glycol.

3. The method for producing a gelatin structure according to claim 1, wherein in the biocompatible material structure forming step, the biocompatible material structure is formed using a biocompatible material including a polyethylene glycol having a molecular weight distribution of more than 2,700 and less than 3,300, a polyethylene glycol having a molecular weight distribution of more than 5,500 and less than 6,500, or a polyethylene glycol having a molecular weight distribution of more than 8,800 and less than 11,200, as the first biocompatible material.

4. The method for producing a gelatin structure according to claim 1, wherein in the biocompatible material structure forming step, a biocompatible material structure having an inclined portion that is inclined with respect to the liquid landing surface is formed by moving the nozzle unit and the substrate relative to each other with respect to a direction of a line normal to the liquid landing surface, which is the surface of the substrate where liquid droplets land, and moving the nozzle unit and the substrate relative to each other in a plane parallel to the liquid landing surface.

5. The method for producing a gelatin structure according to claim 4, wherein in the biocompatible material structure forming step, the inclined portion following a direction having an angle of 60 degrees or more with respect to the liquid landing surface is formed using the first biocompatible material, which has a viscosity of from 4,000 milliPascal·second to 5,000 milliPascal·second, or the third biocompatible material, which has a viscosity of from 500 milliPascal·second to 10,000 milliPascal·second.

6. The method for producing a gelatin structure according to claim 4, wherein in the biocompatible material structure forming step, the inclined portion following a direction having an angle of 30 degrees or more and less than 60 degrees with respect to the liquid landing surface is formed using the third biocompatible material having a viscosity of from 2,000 milliPascal·second to 10,000 milliPascal·second.

7. The method for producing a gelatin structure according to claim 4, wherein in the biocompatible material structure forming step, the biocompatible material structure having a vertical part along the direction of a line normal to the liquid landing surface of the substrate is formed by moving the nozzle unit and the substrate relative to each other in the direction of the line normal to the liquid landing surface.

8. The method for producing a gelatin structure according to claim 7, wherein in the biocompatible material structure forming step, the biocompatible material structure having a horizontal part along a direction orthogonally intersecting the direction of formation of the vertical part is formed by moving the nozzle unit and the substrate relative to each other in a direction orthogonally intersecting the direction of formation of the vertical part.

9. The method for producing a gelatin structure according to claim 1, wherein in the biocompatible material structure forming step, the biocompatible material structure is formed using the first biocompatible material having a viscosity of from 100 milliPascal·second to 5,000 milliPascal·second in a temperature range of from 60° C. to 130° C.

10. The method for producing a gelatin structure according to claim 1, wherein in the biocompatible material structure forming step, the biocompatible material structure is formed using the third biocompatible material having a viscosity of from 100 milliPascal·second to 10,000 milliPascal·second in a temperature range of from 100° C. to 130° C.

11. The method for producing a gelatin structure according to claim 1, wherein in the biocompatible material structure forming step, the biocompatible material structure is formed by stacking the biocompatible material in the droplet state on the substrate having the liquid landing surface that is hydrophilic with respect to the biocompatible material.

12. The method for producing a gelatin structure according to claim 1, wherein in the biocompatible material structure forming step, the biocompatible material structure is formed by stacking the biocompatible material in the droplet state on the substrate having the liquid landing surface that is hydrophobic with respect to the biocompatible material.

13. The method for producing a gelatin structure according to claim 1, further comprising:
a drying step of eliminating at least a portion of water held by the gelatin structure.

14. The method for producing a gelatin structure according to claim 1, wherein the coating film forming step includes a particulate gelatin spraying step of spraying particulate gelatin on the surface of the biocompatible material structure, and a humidifying step of humidifying the biocompatible material structure having the particulate gelatin sprayed on the surface, by applying the conditions of a temperature range and a humidity range, in which at least a portion of the biocompatible material structure is dissolved, and the conditions of a temperature range and a humidity range, in which at least a portion of the particulate gelatin is dissolved.

15. The method for producing a gelatin structure according to claim 1, wherein in the dissolving step, the biocompatible material structure is subjected to the action of water originating from the gelatin to dissolve at least a portion of the biocompatible material structure, and thereby transferring the shape of the biocompatible material structure to the interior of the gelatin structure.

16. The method for producing a gelatin structure according to claim 1, wherein the gelatin is natural gelatin or a recombinant peptide.

* * * * *